US 9,131,875 B2

(12) United States Patent
Bauer et al.

(10) Patent No.: US 9,131,875 B2
(45) Date of Patent: *Sep. 15, 2015

(54) DEVICES AND METHODS FOR CERVIX MEASUREMENT

(71) Applicant: CerviLenz Inc., Chagrin Falls, OH (US)

(72) Inventors: Jonathan P. Bauer, Cincinnati, OH (US); Dean R. Koch, Chagrin Falls, OH (US); Paul E. McCreadie, Ann Arbor, MI (US); Michael Glenn Ross, Los Angeles, CA (US); Craig B. Berky, Milford, OH (US)

(73) Assignee: Cervilenz Inc., Chagrin Falls, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/524,769

(22) Filed: Oct. 27, 2014

(65) Prior Publication Data
US 2015/0094620 A1 Apr. 2, 2015

Related U.S. Application Data

(63) Continuation of application No. 13/954,735, filed on Jul. 30, 2013, now Pat. No. 8,870,794, which is a continuation of application No. 13/747,331, filed on Jan. 22, 2013, now Pat. No. 8,517,960, which is a
(Continued)

(51) Int. Cl.
A61B 1/303 (2006.01)
A61B 5/107 (2006.01)
A61B 5/00 (2006.01)

(52) U.S. Cl.
CPC ............... A61B 5/1076 (2013.01); A61B 5/435 (2013.01); A61B 1/303 (2013.01)

(58) Field of Classification Search
CPC ....... A61B 5/435; A61B 5/1076; A61B 1/303

USPC ........... 600/587, 588, 590, 591, 593; 33/511, 33/512
See application file for complete search history.

(56) References Cited

U.S. PATENT DOCUMENTS 763,076 A 6/1904 Spalding
2,527,168 A 10/1950 Wehler
(Continued)

FOREIGN PATENT DOCUMENTS

GB 2035097 A 6/1980
GB 2162751 A 2/1986
(Continued)

OTHER PUBLICATIONS

Andersen et al.; Prediction of risk for preterm delivery by ultrasonographic measurement of cervical length; Am. J. Obstet. Gynecol.; vol. 163; No. 3; pp. 859-867; Sep. 1990.
(Continued)

Primary Examiner — Max Hindenburg
Assistant Examiner — Jonathan M Foreman
(74) Attorney, Agent, or Firm — Shay Glenn LLP

(57) ABSTRACT

A device for measuring a length of a cervix includes an elongate measurement member extending along a longitudinal axis and including a measurement scale thereon, a hollow member coaxial with and disposed over the elongate measurement member, a flange offset from the longitudinal axis and attached to a distal end of the hollow member, a handle attached to a proximal end of the measurement member, and a locking mechanism on the handle. The hollow member is freely rotatable about the longitudinal axis relative to the measurement member to place the flange in a first position and in a second position perpendicular to the first position without moving the measurement scale. The locking mechanism is configured, when locked, to fix the hollow member relative to the measurement member and, when unlocked, to allow the hollow member to slide axially along the measurement member in the first and second positions.

19 Claims, 18 Drawing Sheets

Related U.S. Application Data continuation of application No. 12/944,580, filed on Nov. 11, 2010, now Pat. No. 8,366,640.

(60) Provisional application No. 61/260,520, filed on Nov. 12, 2009, provisional application No. 61/369,523, filed on Jul. 30, 2010.

(56) References Cited

U.S. PATENT DOCUMENTS

| | | |
|---|---|---|
| 2,587,799 A | 3/1952 | Winter |
| 2,807,088 A | 9/1957 | Salzman et al. |
| 3,381,387 A | 5/1968 | Landrum, Jr. |
| 3,501,839 A | 3/1970 | Bancescu et al. |
| 3,630,190 A | 12/1971 | Baker |
| 3,706,307 A | 12/1972 | Hasson |
| 3,744,481 A | 7/1973 | McDonald |
| 3,913,561 A | 10/1975 | Maeda |
| 4,016,867 A | 4/1977 | King et al. |
| 4,121,572 A | 10/1978 | Krzeminski |
| 4,224,951 A | 9/1980 | Hasson |
| 4,248,214 A | 2/1981 | Hannah et al. |
| 4,489,732 A | 12/1984 | Hasson |
| 4,500,313 A | 2/1985 | Young |
| 4,544,231 A | 10/1985 | Peterson |
| 4,574,794 A | 3/1986 | Cooke et al. |
| 4,644,660 A | 2/1987 | Mathes |
| 4,685,474 A | 8/1987 | Kurz et al. |
| 4,782,595 A | 11/1988 | Diewert |
| 5,013,318 A | 5/1991 | Spranza, III et al. |
| 5,034,009 A | 7/1991 | Mouchel |
| 5,122,146 A | 6/1992 | Chapman et al. |
| 5,135,006 A | 8/1992 | Bellinson |
| 5,165,789 A | 11/1992 | Womack |
| 5,186,180 A | 2/1993 | Bellas |
| 5,370,640 A | 12/1994 | Kolff |
| 5,657,764 A | 8/1997 | Coulter et al. |
| 5,658,295 A | 8/1997 | Krementsov |
| 5,722,426 A | 3/1998 | Kolff |
| 5,876,357 A | 3/1999 | Tomer |
| 5,980,804 A | 11/1999 | Koch |
| 6,039,701 A | 3/2000 | Sliwa et al. |
| 6,231,568 B1 | 5/2001 | Loeb et al. |
| 6,419,646 B1 | 7/2002 | Baxter-Jones |
| 6,450,976 B2 | 9/2002 | Korotko et al. |
| 6,450,977 B1 | 9/2002 | Baxter-Jones |
| 6,468,232 B1 | 10/2002 | Ashton-Miller et al. |
| 6,524,259 B2 | 2/2003 | Baxter-Jones et al. |
| 6,802,817 B2 | 10/2004 | Baxter-Jones et al. |
| 6,994,678 B2 | 2/2006 | Baxter-Jones et al. |
| 8,366,640 B2 | 2/2013 | Bauer et al. |
| 8,517,960 B2 | 8/2013 | Bauer et al. |
| 8,870,794 B2 | 10/2014 | Bauer et al. |
| 2006/0020230 A1 | 1/2006 | Baxter-Jones et al. |
| 2007/0142752 A1 | 6/2007 | Kotmel et al. |
| 2008/0021350 A1 | 1/2008 | Bechtle et al. |
| 2010/0331601 A1 | 12/2010 | Partridge et al. |

FOREIGN PATENT DOCUMENTS

| | | |
|---|---|---|
| JP | 4197236 | 7/1992 |
| JP | 5505548 | 8/1993 |
| JP | 3122384 U | 5/2006 |
| WO | WO01/76477 A1 | 10/2001 |
| WO | WO02/100270 A1 | 12/2002 |

OTHER PUBLICATIONS

Anderson et al.; Relationship between length of gestation and cervical dilatation, uterine contractility, and other factors during pregnancy; Am. J. Obst. & Gynec.; vol. 105; No. 8; pp. 1207-1214; Dec. 15, 1969.

Brook et al.; Ultrasonography in the Diagnosis of Cervical Incompetence in Pregnancy—A New Diagnostic Approach; British Journal of Obstetrics and Gynecology; vol. 88; pp. 640-643; Jun. 1981.

Burwick et al.; Cervilenz assessment of cervical length compared to fetal fibronectin in prediction of preterm delivery in women with threatened preterm labor; J. of Maternal-Fetal and Neonatal Medicine; Online (Informa Healthcare); pp. 1-5; Nov. 11, 2010.

Heath et al.; Cervical length at 23 weeks of gestation: prediction of spontaneous preterm delivery; Ultrasound Obstet. Gynecol.; vol. 12; pp. 312-317; Nov. 1998.

Hologic, Inc.; NovaSure®—SureSound Uterine Cavity Measuring Device; http://www.novasure.com/novasure-procedure/suresound-uterine-cavity-measuring-device.cfm; (printed Jul. 12, 2010).

Iams et al.; The length of the cervix and the risk of spontaneous premature delivery; N. Eng. J. Med.; vol. 334; No. 9; pp. 567-572; Feb. 29, 1996.

Michaels et al.; Ultrasound differentiation of the competent from the incompetent cervix: Prevention of preterm delivery; Am. J. Obstet Gynecol.; vol. 154; No. 3; pp. 537-546; Mar. 1986.

Norwitz et al.; The Control of Labor; New Eng. J. of Med.; vol. 341; No. 9; pp. 660-666; Aug. 1999.

Nzeh et al.; Sonographic assessment of the incompetent cervix in pregnancy; Int. J. Gynecol. Obstet.; vol. 37; pp. 179-184; Mar. 1992.

Rush et al.; Contribution of preterm delivery to perinatal mortality; British Medical Journal; vol. 2; pp. 965-968; Oct. 23, 1976.

Sarti et al.; Ultrasonic Visualization of a Dilated Cervix During Pregnancy; Radiology; vol. 130; pp. 417-420; Feb. 1979.

Sonek et al.; Preterm Birth, Causes, Prevention and Management; Second Edition; Chapter 5; McGraw-Hill, Inc.; pp. 137-160; Jan. 1993.

Stubblefield; Preterm Birth, Causes, Prevention, and Management; Second Edition; Chapter 1; McGraw-Hill, Inc.; pp. 3-39; Jan. 1993.

Charles et al., Preterm Birth: Causes, Prevention, and Management; Chapter 6 (Cervical Incompetence), pp. 98-111 (year of pub. sufficiently earlier than effective US filed and any foreign priority date) 1984.

Vaalamo et al.; The Incompetent Cervix During Pregnancy Diagnosed by Ultrasound; Acta Obstet. Gynecol Scand; vol. 62; pp. 19-21; (year of pub. sufficiently earlier than effective US filed and any foreign priority date) 1983.

Villar et al.; Pre-term delivery syndrome: the unmet need; Res. Clin. Forums; vol. 16; No. 3; pp. 9-33; (year of pub. sufficiently earlier than effective US filed and any foreign priority date)1994.

Wood et al.; The prediction of premature labor by observation of the cervix and external tocography; Am. J. Obst. & Gynec.; vol. 91; No. 3; pp. 396-402; Feb. 1965.

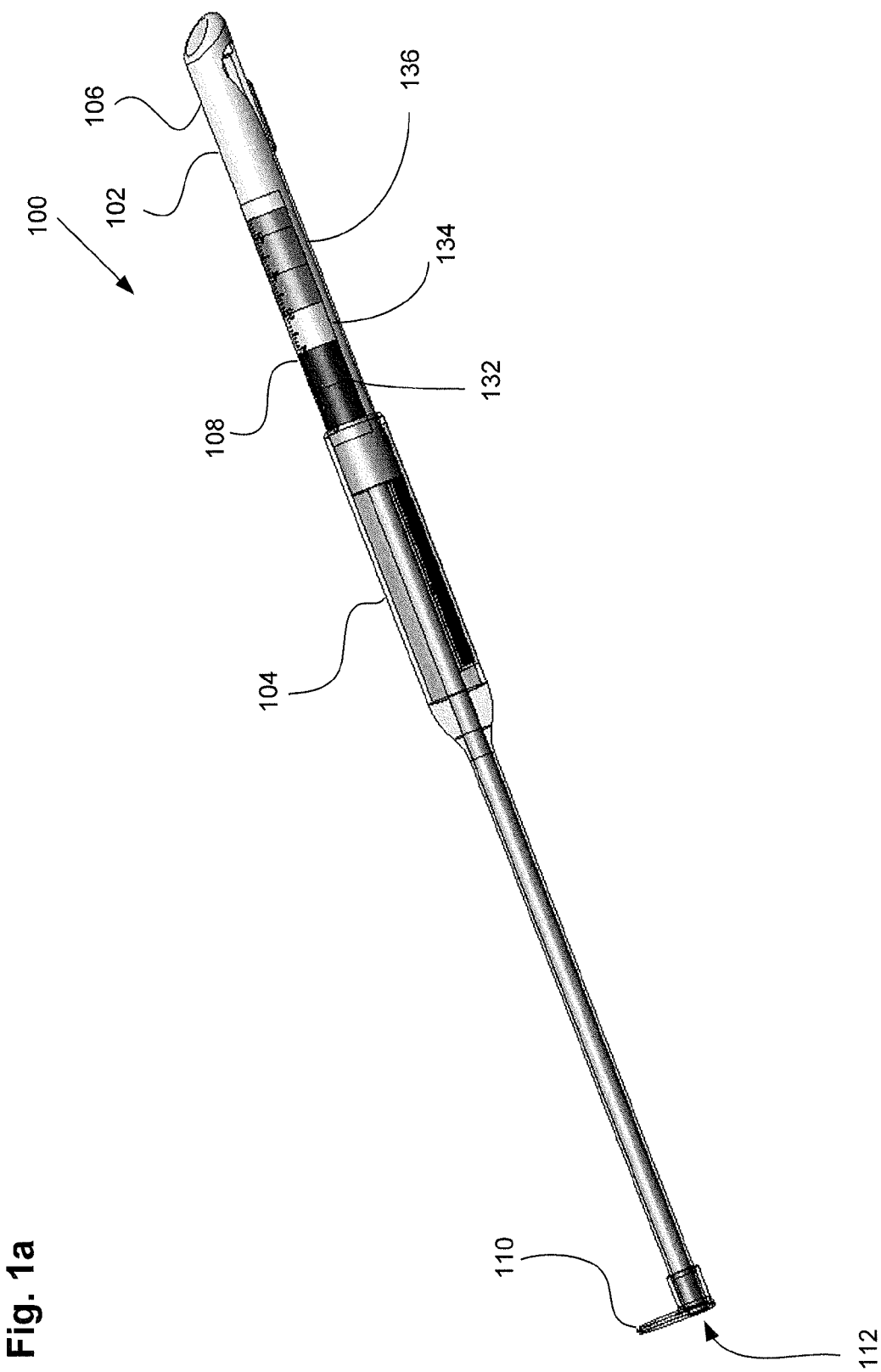

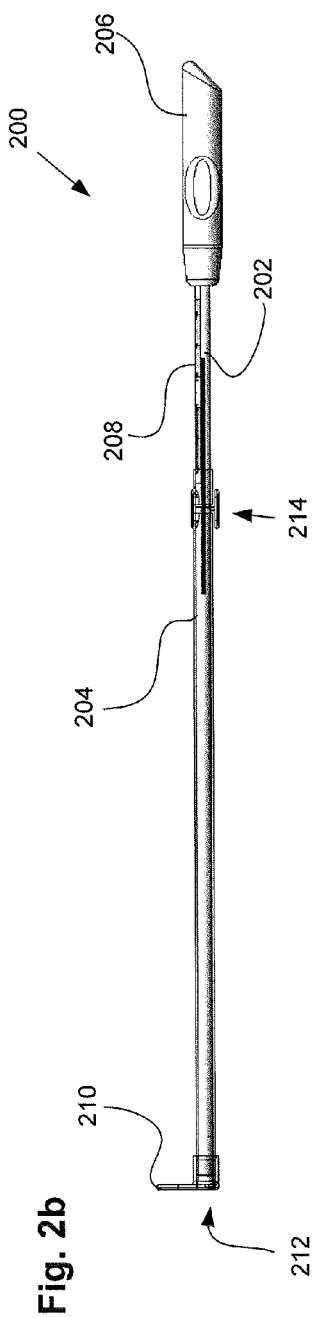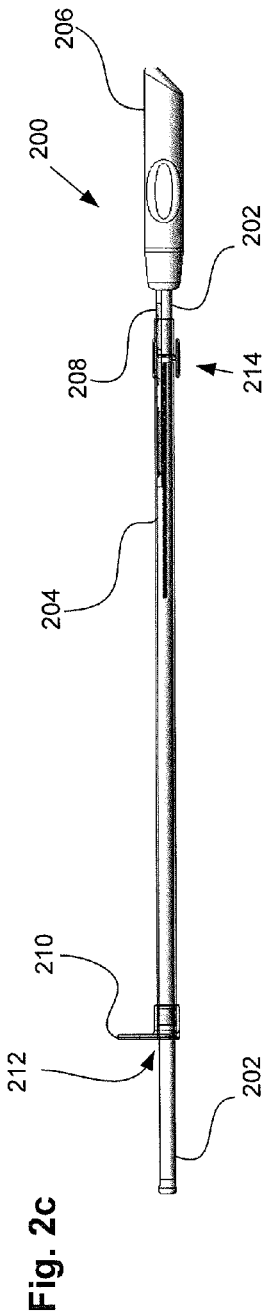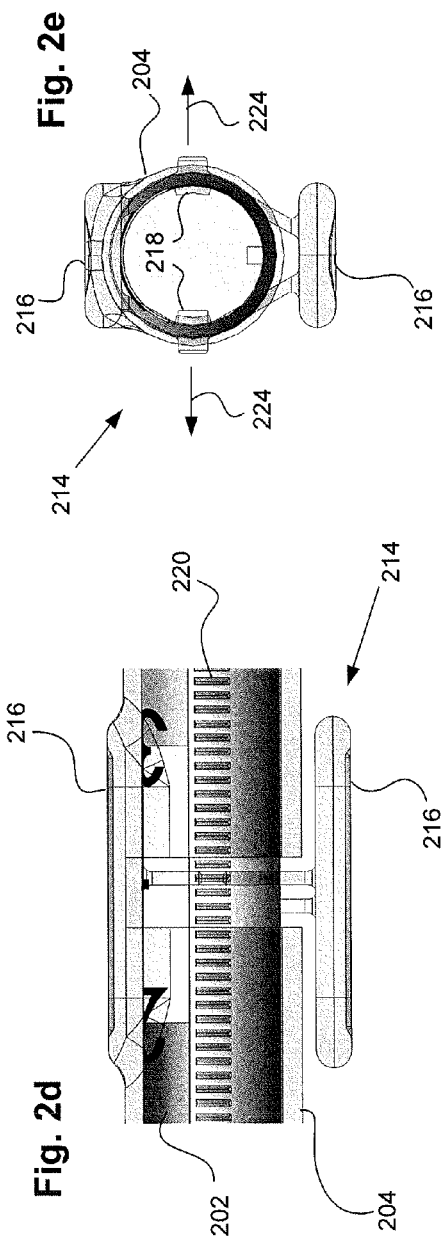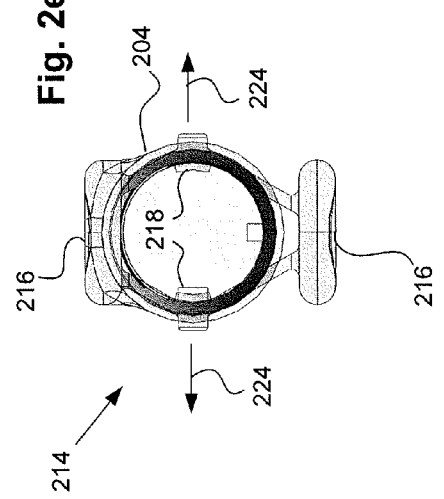

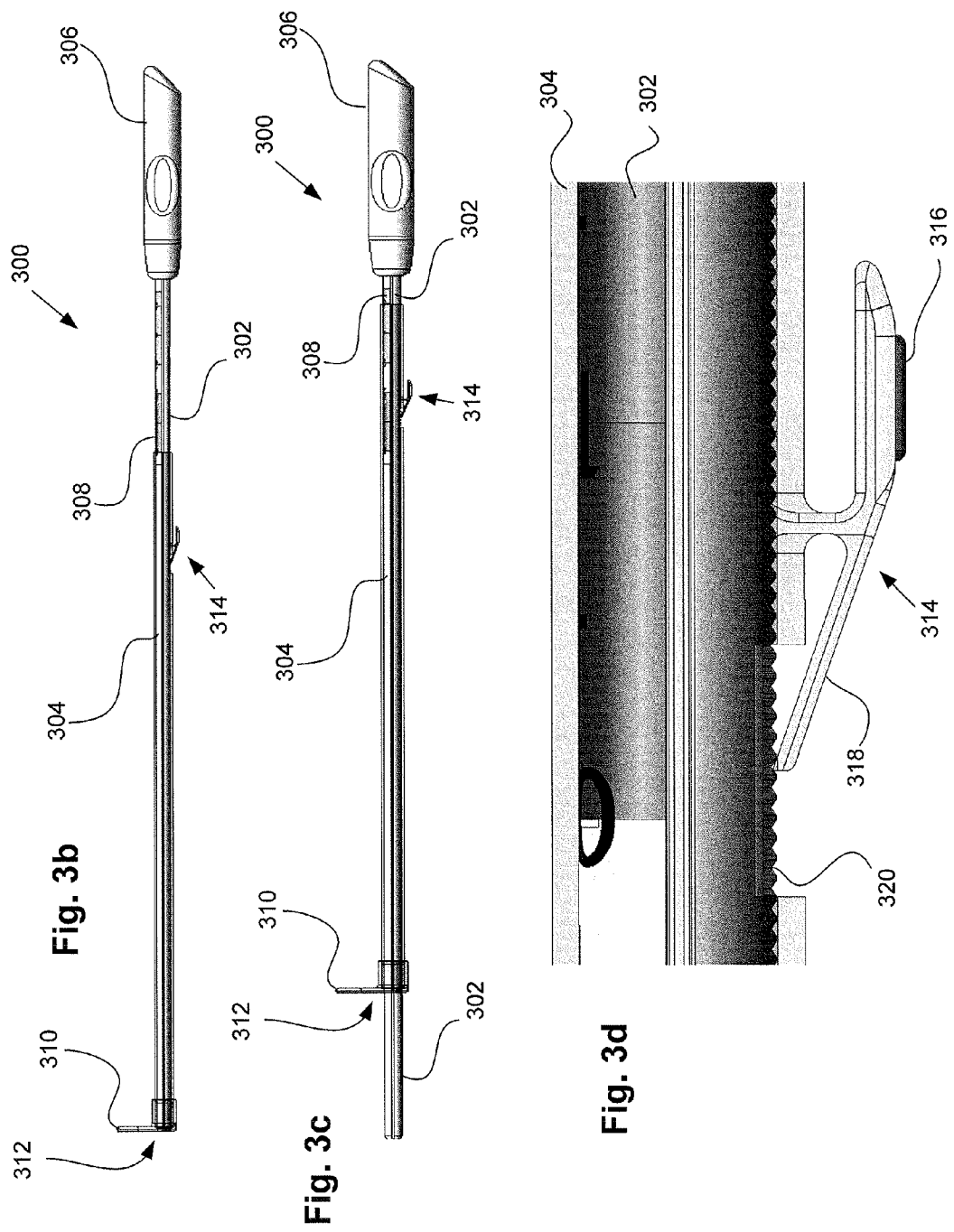

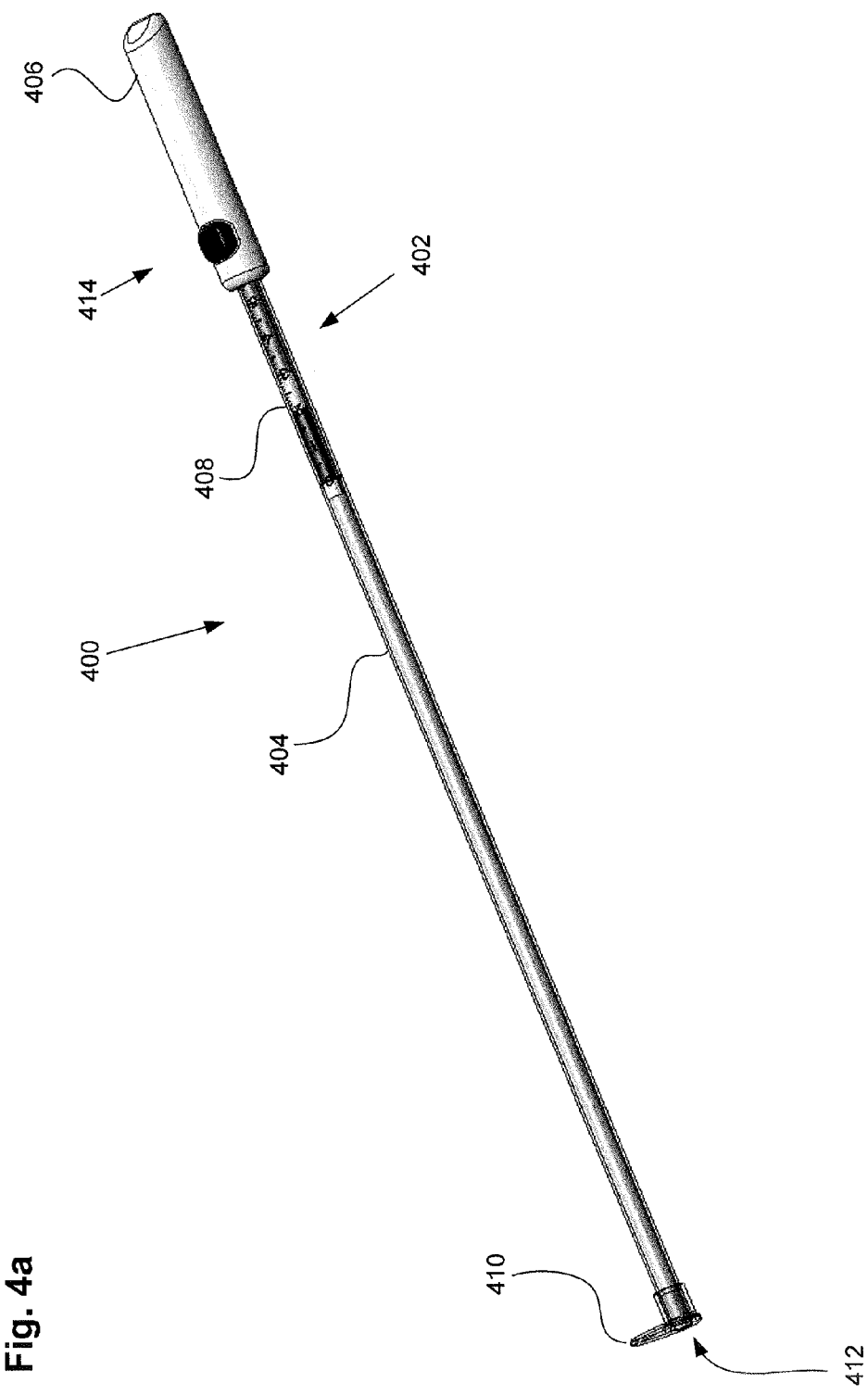

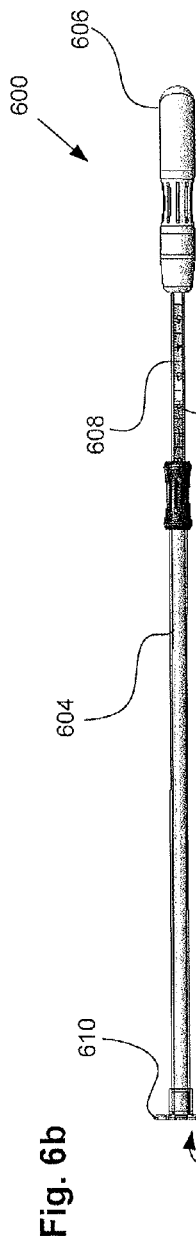
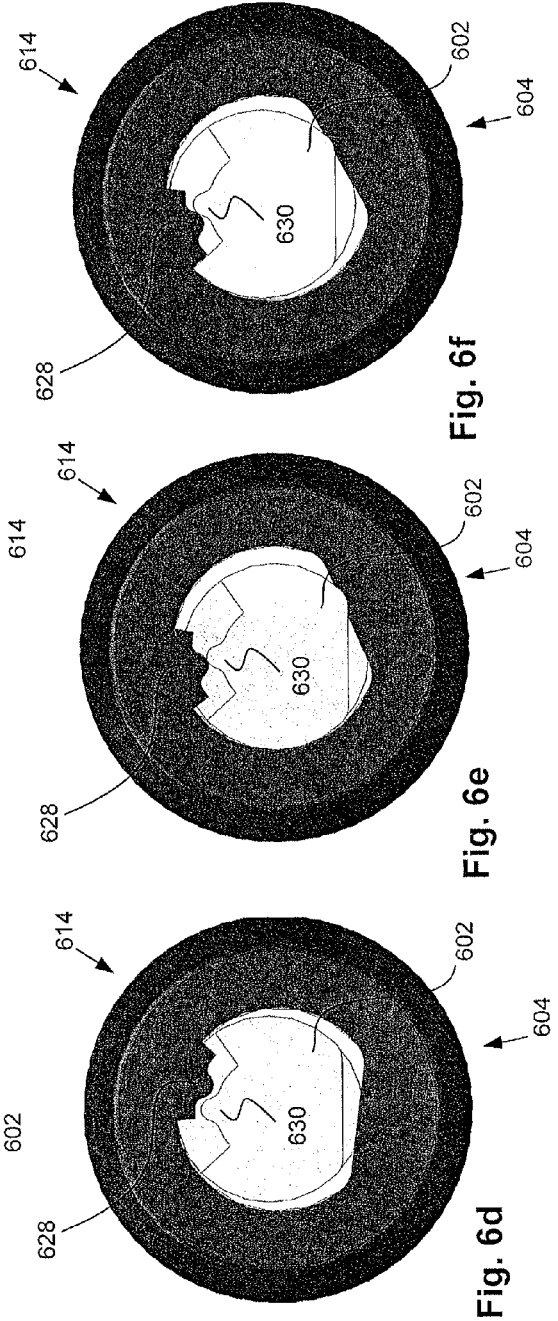
Fig. 6b  Fig. 6c  Fig. 6d  Fig. 6e  Fig. 6f

DEVICES AND METHODS FOR CERVIX MEASUREMENT

CROSS REFERENCE TO RELATED APPLICATIONS

This application is a continuation of U.S. patent application Ser. No. 13/954,735, filed on Jul. 30, 2013, titled "DEVICES AND METHODS FOR CERVIX MEASUREMENT," now U.S. Pat. No. 8,870,794, which is a continuation of U.S. patent application Ser. No. 13/747,331, filed on Jan. 22, 2013, titled "DEVICES AND METHODS FOR THE CERVIX MEASUREMENT," now U.S. Pat. No. 8,517,960, which is a continuation of U.S. patent application Ser. No. 12/944,580, filed on Nov. 11, 2010, titled "DEVICES AND METHODS FOR CERVIX MEASUREMENT," now U.S. Pat. No. 8,366,640, which claims priority to U.S. Provisional Patent Application No. 61/260,520, filed Nov. 12, 2009, entitled "DEVICES AND METHODS FOR CERVIX MEASUREMENT" and U.S. Provisional Patent Application No. 61/369,523, filed Jul. 30, 2010, titled "DEVICES AND METHODS FOR CERVIX MEASUREMENT." These applications are herein incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates to medical devices and methods of using such devices. More particularly, the invention relates to instruments and methods to measure the length of the cervix in the fornix vaginae and the dilation of the cervix uteri.

BACKGROUND

Preterm labor, or labor before 37 weeks gestation, has been reported in approximately 12.8 percent of all births but accounts for more than 85 percent of all perinatal complications and death. Rush et al., BMJ 2:965-8 (1976) and Villar et al., Res. Clin. Forums 16:9-33 (1994), which are both incorporated herein by reference. An inverse relationship between cervical length in the fornix vaginae and the risk of preterm labor has also been observed. Andersen et al., Am. J. Obstet. Gynecol. 163:859 (1990); Iams et al., N. Eng. J. Med. 334: 567-72 (1996) and Heath et al., and Ultrasound Obstet. Gynecol. 12:312-7 (1998), which all are incorporated herein by reference. Accordingly, many physicians find it useful to examine the cervix in the fornix vaginae as part of normal prenatal care in order to assess risk of preterm labor.

It has long been known that the cervix normally undergoes a series of physical and biochemical changes during the course of pregnancy, which enhance the ease and safety of the birthing process for the mother and baby. For example, in the early stages of labor the tissues of the cervical canal soften and become more pliable, the cervix shortens (effaces), and the diameter of the proximal end of the cervical canal begins to increase at the internal os. As labor progresses, growth of the cervical diameter propagates to the distal end of the cervical canal, toward the external os. In the final stages of labor, the external os dilates allowing for the unobstructed passage of the fetus.

In addition to the physical and biochemical changes associated with normal labor, genetic or environmental factors, such as medical illness or infection, stress, malnutrition, chronic deprivation and certain chemicals or drugs can cause changes in the cervix. For example, it is well known that the in utero exposure of some women to diethylstilbestrol (DES) results in cervical abnormalities and in some cases gross anatomical changes, which leads to an incompetent cervix where the cervix matures, softens and painlessly dilates without apparent uterine contractions. An incompetent cervix can also occur where there is a history of cervical injury, as in a previous traumatic delivery, or as a result of induced abortion if the cervix is forcibly dilated to large diameters. Details of the incompetent cervix are discussed in Sonek, et al., Preterm Birth, Causes, Prevention and Management, Second Edition, McGraw-Hill, Inc., (1993), Chapter 5, which is incorporated by reference herein.

Cervical incompetence is a well recognized clinical problem. Several investigators have reported evidence of increased internal cervical os diameter as being consistent with cervical incompetence (see Brook et al., J. Obstet. Gynecol. 88:640 (1981); Michaels et al., Am. J. Obstet. Gynecol. 154:537 (1986); Sarti et al., Radiology 130:417 (1979); and Vaalamo et al., Acta Obstet. Gynecol. Scan 62:19 (1983), all of which are incorporated by reference herein). Internal os diameters ranging between 15 mm to 23 mm have been observed in connection with an incompetent cervix. Accordingly, a critical assessment in the diagnosis of an incompetent cervix involves measurement of the internal cervical os diameter.

There are also devices and methods to measure the diameter of the external cervical os. For example, cervical diameter can be manually estimated by a practitioner's use of his or her digits. Although an individual practitioner can achieve acceptable repeatability using this method, there is a significant variation between practitioners due to the subjective nature of the procedure. To address these concerns, various monitoring and measuring devices and methods have been developed. For example, an instrument for measuring dilation of the cervix uteri is described in U.S. Pat. No. 5,658,295. However, this device is somewhat large, leading to a risk of injury to the fundus of the vagina or cervical os. Additionally, it is not disposable and requires repeated sterilization. Another device for measuring cervical diameter is described, for example, in U.S. Pat. No. 6,039,701. In one version, the device described therein has a loop element which is secured to the cervix. The loop expands or contracts with the cervix and a gauge is coupled to the loop for measuring changes in the loop dimension. Such changes can then be detected by electronic means. Accordingly, this device is rather complex and expensive to manufacture.

Even if a woman is found to have an apparently normal internal cervical os diameter, there may nonetheless be a risk for preterm labor and delivery. Currently, risk assessment for preterm delivery remains difficult, particularly among women with no history of preterm birth. However, the findings that preterm delivery is more common among women with premature cervical shortening or effacement suggest that a measuring the length of the cervix would be predictive for preterm labor.

Currently, a physician has at least two options to measure the length of the cervix in the fornix vaginae. One such method involves serial digital examination of the cervix by estimating the length from the external cervical os to the cervical-uterine junction, as palpated through the vaginal fornix. Although this is useful for general qualitative analysis, it does not afford an easy nor accurate measurement of the length of the cervix from the external cervical os to the cervical-uterine junction (also described herein as the length of the cervix extending into the vagina) and, therefore, does not provide an accurate assessment of the risk of preterm labor. Despite the use of gloves, digital vaginal exams always carry with them the risk of transmitting infectious agents, especially to the fetal membranes, the lining and/or muscle of the uterus, or to the fetus itself.

Another method involves real-time sonographic evaluation of the cervix. This method provides relatively quick and accurate cervical dimensions. However, it requires expensive equipment, highly skilled operators, as well as skill in interpretation of results, which are all subject to human error. Additionally, there is a risk that the probe that must be inserted into the vagina as part of the procedure may cause injury if not inserted with care. Also, due to the expense of the procedure many women, especially those without proper health insurance, cannot afford to have a sonographic test performed.

It would be beneficial if there were an instrument a practitioner could use to measure the cervix quickly and accurately, and with little material expense. Although there are several instruments available for determining various dimensions of the uterus, there is no suitable instrument for measuring the length of the cervix in the fornix vaginae. For example, U.S. Pat. No. 4,016,867 describes a uterine caliper and depth gauge for taking a variety of uterine measurements, which although useful for fitting an intrauterine contraceptive device, is not capable of measuring the length of the cervix in the fornix vaginae due to interference by the caliper's wings. In fact, similar devices described in U.S. Pat. Nos. 4,224,951; 4,489,732; 4,685,474; and 5,658,295 suffer from similar problems due to their use of expandable wings or divergeable probe tips. These devices are also relatively sophisticated, making them expensive to manufacture and purchase. U.S. Pat. No. 3,630,190 describes a flexible intrauterine probe, which is particularly adapted to measuring the distance between the cervical os and the fundus of the uterus. The stem portion of the device has a plurality of annular ridges spaced apart from each other by a predetermined distance, preferably not more than one-half inch apart. However, this device is not adapted for accurately measuring the length of the cervix in the fornix vaginae because of the lack of an appropriate measuring scale and a stop for automatically recording the measurement.

There exists a need for a simple and inexpensive device that can be used to determine the length of the cervix in the fornix vaginae and, thus, predict the risk of preterm labor, as well as other conditions. There is also a need for such a device that can measure the dilation of the cervix uteri, to provide an overall assessment of the cervix and to determine the particular stage of labor. Ideally, the device should be adapted for use by a physician or obstetrician or even a trained nurse in the doctor's office or clinic. Preferably, the device should be sterile and disposable. In addition, it is desirable that device be able to lock after a measurement is taken to ensure that the measurement does not change between the time a user takes the measurement and removes the device from the patient to read the measurement. The present invention satisfies these needs and provides related advantages as well.

SUMMARY OF THE DISCLOSURE

In general, in one aspect, a device for measuring a length of a cervix includes an elongate measurement member, a hollow member, a flange, a handle, and a locking mechanism. The elongate measurement member extends along a longitudinal axis and includes a measurement scale thereon. The hollow member is coaxial with and disposed over the elongate measurement member. The flange is offset from the longitudinal axis and attached to a distal end of the hollow member. The handle is attached to a proximal end of the measurement member. The locking mechanism is configured, when locked, to fix the hollow member relative to the measurement member and, when unlocked to allow the hollow member to slide along the measurement member and rotate about the longitudinal axis so as to place the flange in a desired position without moving the measurement scale.

This and other embodiments can include one or more of the following features. The proximal end of the hollow member can be slideable into the handle. The flange can have an opening through which the measurement member can advance distally. The flange can have a flat surface perpendicular to the longitudinal axis. The locking mechanism can include a button, the button including a through-hole configured such that the hollow member can slide therethrough and a lock channel configured such that the hollow member cannot slide therethrough. The button can further include at least one lock ramp between the through-hole and the lock channel. The measurement scale can be a millimeter scale. The measurement scale can extend from 0 mm to 50 mm. The hollow member can be transparent. The measurement scale can include an opaque background. The device can further include an indicator line on the hollow member. The indicator line can be a color other than black.

In general, in one aspect, a method for measuring a length of a cervix includes: holding a handle of a device, the device further including an elongate measurement member having a measurement scale thereon, a hollow member coaxial with and disposed over the elongate measurement member, and a flange attached to a distal end of the hollow member; rotating the hollow member about the elongate measurement member so as to place the flange at a desired orientation without rotating the measurement scale; advancing the device distally within a vagina until the flange contacts a cervix at an external uterine opening; advancing the measurement member distally within the vagina until a distal end of the measurement member contacts a cervical uterine junction at a fornix vaginae; locking the measurement member relative to the hollow member by locking a locking mechanism on the handle; and observing a position of the hollow member with respect to the measurement member to determine a length of the cervix in the fornix vaginae.

This and other embodiments can include one or more of the following features. Advancing the measurement member distally can include sliding the hollow member into the handle. The flange can be offset from a longitudinal axis of the measurement member. The locking mechanism can include a button having a through-hole and a lock channel, and wherein locking the locking mechanism comprises pushing the button such that the hollow member moves into the lock channel and cannot slide through the through-hole. Observing the position can include observing an indicator line on the hollow member with respect to a measurement scale on the measurement member. The method can further include determining the risk of miscarriage based upon the length of the cervix in the fornix vaginae, wherein the length of the cervix in the fornix vaginae is inversely related to the risk of miscarriage. The method can further include predicting the ease of inducing labor, wherein the length of the cervix in the fornix vaginae is inversely related to the ease of inducing labor. The method can further include determining the risk of preterm labor based upon the length of the cervix in the fornix vaginae, wherein the length of the cervix in the fornix vaginae is inversely related to the risk of preterm labor.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1a is an illustration of a measuring device, according to one embodiment.

FIGS. 1b-1e are additional views of the measuring device of FIG. 1a.

FIGS. 2b-2e are additional views of the measuring device of FIG. 2a.

FIGS. 3b-3d are additional views of the measuring device of FIG. 3a.

FIG. 4a is an illustration of a measuring device, according to one embodiment.

FIGS. 4b-4g are additional views of the measuring device of FIG. 4a.

FIGS. 5b-5d are additional views of the measuring device of FIG. 5a.

FIGS. 6b-6f are additional views of the measuring device of FIG. 6a.

FIGS. 7b-7h are additional views of the measuring device of FIG. 7a.

DETAILED DESCRIPTION

Figure 1B:
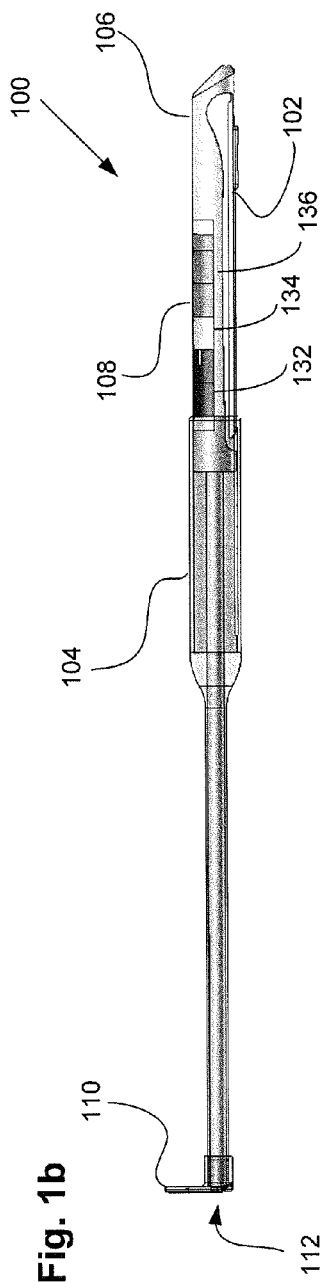

The present invention provides various devices and methods for determining dimensions of female reproductive organs. For example, the devices described herein are particularly adapted for determining the length of the cervix in the fornix vaginae, which, as described above, is related to the risk of preterm labor in an individual. The devices can also be suited for determining the dilation of the cervix uteri, for predicting the risk of preterm labor or the particular stage of delivery.

It is, however, contemplated herein, that the invention is not limited to determining various dimensions of female reproductive organs. For example, the invention can be usable for determining the dimension of any body cavity or passageway where such a device would be insertable, such as a vagina, uterus, mouth, throat, nasal cavity, ear channel, rectum, and also to any cavity created and opened by surgery, for example, during chest, abdominal or brain surgery.

The devices described herein are also preferably fabricated from relatively inexpensive materials and the measurement is quick to perform. This allows the practitioner to repeat the test over time and therefore to more closely monitor a woman's pregnancy and risk for preterm labor. It is also contemplated that the device can record the various measurements automatically, where the only input required by the practitioner is the proper insertion of the device into the body cavity or passageway. This can be accomplished by the use of a flange to stop progression of the hollow member of the device while still allowing the measurement member to be advanced within the body.

FIG. 1a illustrates a measuring device 100 that includes an elongated measurement member 102 and an elongated hollow member 104. The elongated measurement member 102 is adapted to be inserted into the hollow member 104, and specifically into a lumen of the hollow member. Handle 106 can be positioned on a proximal portion of the measuring device, as shown in FIG. 1a. In one embodiment, the handle is molded from the same material as the measurement member 102. In other embodiments, the handle can be a rubber or foam component that is fitted on to and over the proximal end of the measuring device.

A measurement scale 108 can be disposed along a portion of the measurement member 102. The measurement scale 108 can include any number of a series of visual markings on the measurement member 102 which relate a measurement or distance. In a particularly preferred embodiment, the measurement scale 108 includes a plurality of millimeter (mm) incremental markings and a plurality of centimeter (cm) incremental markings.

As shown in FIG. 1a, the measurement scale 108 can be color-coded to indicate the relative risks of preterm delivery for a cervix length falling within each respective colored region. For example, in one embodiment, a first zone 132 can include the incremental markings less than 2 cm and can be coded in a first color, such as red, a second zone 134 can include the incremental markings from 2 to 3 cm and can be coded in a second color, such as yellow, and the third zone 134 can include the incremental markings from 3 to 5 cm and can be coded in a third color, such as green. In FIG. 1a, the measurement scale is color-coded into three regions that each visually represents the relative risks of preterm delivery for a cervix length falling within the respective region. For instance, the first zone 132 indicates a shorter cervix, and therefore a higher risk of preterm delivery, than the second zone 134, which indicates a cervix length that reflects a higher risk of preterm delivery than the green zone 136.

A flange 110 that is shaped for non-abrasive contact with tissue can be disposed on a distal portion of measuring device 100. The flange can be preferably flat and spherically or conically shaped. Alternatively, however, the flange may be any other non-abrasive shape to reduce irritation and scraping of the cervical canal, fundus of the vagina or perforation of the fundus of the uterus. The main body of the flange is also preferably offset from the longitudinal axis of the measuring device 100. Additionally, the flange can include an opening 112 through, which measurement member 102 may be advanced distally after the flange contacts a bodily surface. Preferably, the flange is secured to the distal end of the hollow member 104 using a suitable attachment means, such as, e.g., an adhesive. Alternatively, the flange may be formed as an integral component of the hollow member 104.

Figure 1C:
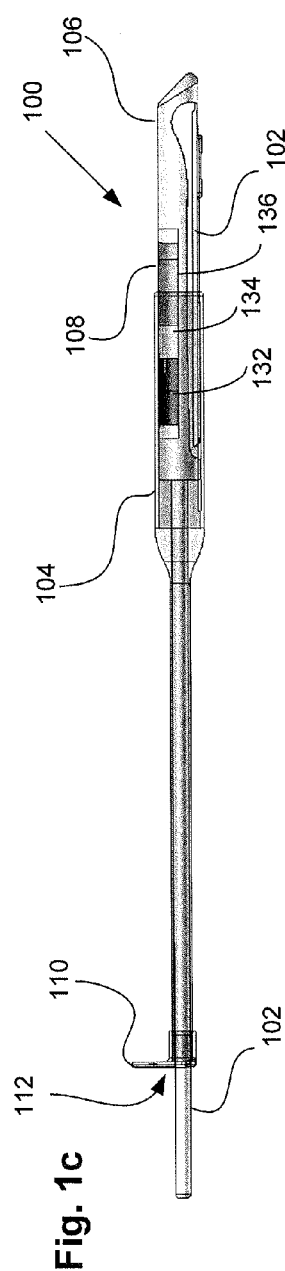
Figure 1D:
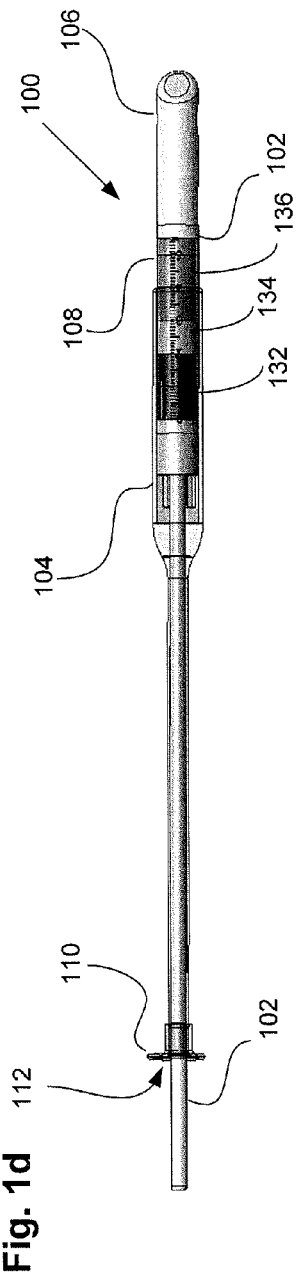

FIGS. 1b-1d illustrate the operation of the measuring device 100 as it is used to measure the length of a cervix. When the distal end of the measurement member 102 is flush with the flange, as shown in FIG. 1b, the device is in a starting configuration. The device 100 can be advanced into the vagina until the flange 110 is placed into contact with the end of the cervix at the external uterine opening. At this point, further forward progress of the hollow member 104 within the cervical canal or further within the body is prevented as a result of the contact between flange 110 and the end of the cervix at the external uterine opening. Since flange 110 is preferably offset from the longitudinal axis of measuring device 100, in one embodiment the flange is placed both in contact with the end of the cervix and also covering the external uterine opening. As a result, the device can oriented so that measurement member 102 is still able to be progressed within the fornix, rather than being advanced through the uterus, since the body of flange 106 is, with this method, covering the external uterine opening.

Subsequently, as shown in FIGS. 1c-1d, a distal portion of measurement member 102 can continue to be advanced through opening 112 of flange 110 until the distal end contacts a wall of the body, such as, e.g., the anterior fornix. When the distal end of the measurement member is advanced beyond the flange the device is in a measuring configuration. FIG. 1c shows a side view of the measurement member in the measuring configuration, and FIG. 1d shows a top down view of the device in the measuring configuration. It can be seen in FIG. 1d, for example, that the measurement member has been advanced 4 cm beyond the flange. The length of the cervix can then be measured by observing the position of the proximal end of the hollow member 104 along the measurement scale 108 of the measurement member 102. In another embodiment, a method of measurement comprises advancing the distal end of the measurement member 102 to the wall of the body, such as the anterior fornix, and then advancing the hollow member 104 so that the flange 110 is placed into contact with the end of the cervix at the external uterine opening.

Figure 1E:
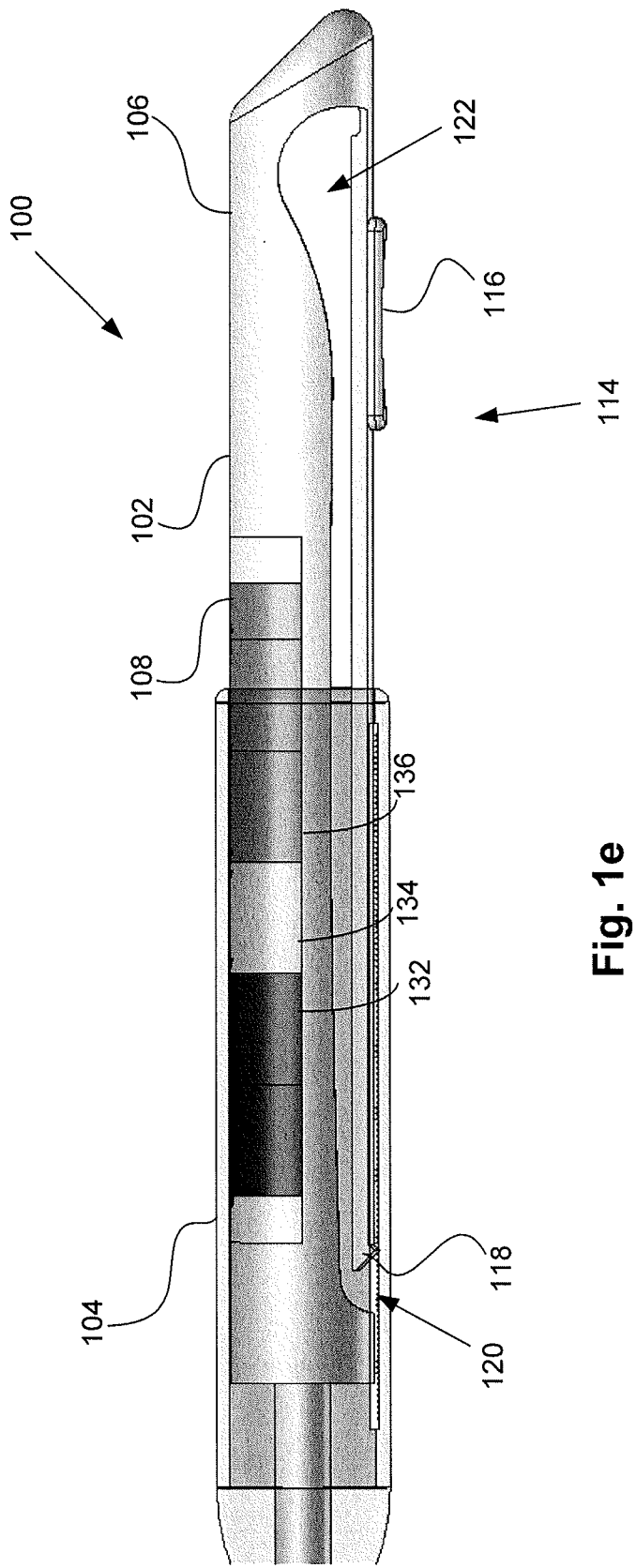

Referring now to FIG. 1e, a locking mechanism 114 can be located on the measuring device 100 that allows a user to secure the measurement member 102 within the hollow member 104 after the measurement of a body part, such as, e.g., the length of the cervix. In FIG. 1e, the locking mechanism 114 includes button 116, cantilever arm 118, detents 120, and opening 122. When the locking mechanism is in the locked configuration, as shown in FIG. 1e, the cantilever arm 118 engages detents 120 on the inside of hollow member 104. The cantilever arm can be integral to the measurement member 102, for example. To allow sliding of the measurement member within the hollow member, button 116 can be pressed inwards towards opening 122, causing cantilever arm 118 to disengage detents 120 and allow sliding.

For example, to take a measurement of a body part, a user can insert the measuring device 100 into the patient. The user can then press the button 116 inwards to disengage the cantilever arm and allow the measurement member to slide within the hollow member. After the measurement of a body part is taken with the device, the user can release the button, causing the cantilever arm to engage the detents and lock the position of the measurement member 102 within the hollow member 104. This allows the user to remove the device from the patient to read the measurement scale while ensuring that movement of the measurement member 102 proximally or distally within the hollow member 104 is prevented.

During a measurement procedure, a user can hold handle 106 with the dominant hand like a dart, and can hold the barrel of the hollow member 104 with the non-dominant hand. The user can activate button 116 with the dominant hand to temporarily unlock the measuring device, allowing the hollow member to slide with respect to the measurement member.

Figure 2A:
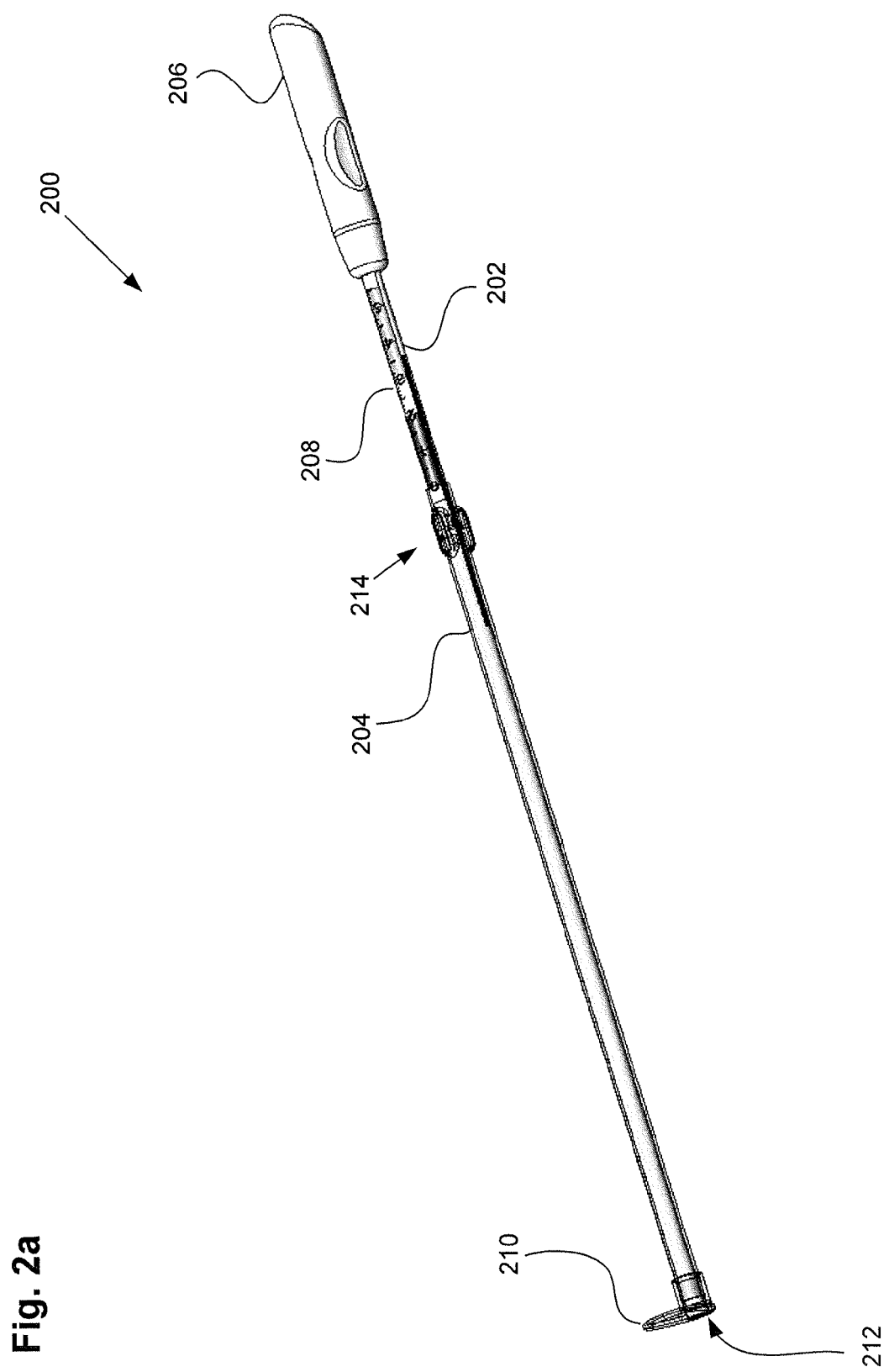
FIG. 2a is an illustration of a measuring device, according to one embodiment.

Referring now to FIG. 2a, another embodiment of a measuring device 200 is shown. Measuring device 200 includes many of the features of measuring device 100, described above and illustrated in FIGS. 1a-1e. For example, measuring device 200 includes an elongated measurement member 202 slidably disposed within an elongated hollow member 204. Handle 206 can be positioned on a proximal portion of the measuring device, and measurement scale 208, such as a color-coded measurement scale, can be disposed on the measurement member 202. The measuring device can further include a flange 210 on a distal portion of the device, and an opening 212 that allows the measurement member 202 to extend distally beyond the hollow member 204.

As described above, the device 200 can have a starting configuration, as shown in FIG. 2b, and a measuring configuration, as shown in FIG. 2c. The measuring device 200 can further include a locking mechanism 214. The locking mechanism allows a user to lock the measurement member 202 within the hollow member 204, to prevent movement of the measurement member with respect to the hollow member after a measurement is taken. In the embodiment shown in FIGS. 2a-2e, the locking mechanism 214 is disposed on the hollow member 204.

Referring now to FIG. 2d, which is a side view of the locking mechanism 214, and FIG. 2e, which is a cross sectional view of the locking mechanism 214, the locking mechanism can further include pads or buttons 216, tabs 218, and detents 220. The buttons 216 and tabs 218 can be integral to the hollow member 204, and the detents 220 can be integral to the measurement member 202, for example. In the embodiment shown in FIGS. 2d-2e, the locking mechanism includes two buttons 216. However, in other embodiments, the locking mechanism can include only a single button, or alternatively, can include more than two buttons.

When the locking mechanism 214 is in a locked configuration, as shown in FIG. 2d, the tabs engage detents 220, preventing any movement of the measurement member with respect to the hollow member 204. However, when the buttons 216 are depressed inwards by a user, as shown in FIG. 2e, the tabs 218 can be squeezed outwards, as indicated by arrows 224, causing them to disengage from detents 220. This allows a measurement to be taken by sliding the measurement member 202 within the hollow member 204.

To take a measurement of a body part, a user can insert the measuring device 200 into the patient. The user can then press the button or buttons 216 inwards to cause the tabs 218 to squeeze outwards disengaging detents 220, thereby allowing the measurement member to slide within the hollow member. After the measurement of a body part is taken with the device, the user can release the buttons, causing the tabs to engage the detents and lock the position of the measurement member 202 within the hollow member 204. This allows the user to remove the device from the patient to read the measurement scale while ensuring that movement of the measurement member 202 proximally or distally within the hollow member 204 is prevented.

During a measurement procedure, a user can hold handle 206 with the dominant hand like a dart, and can hold the barrel of the hollow member 204 with the non-dominant hand. The user can activate button 216 with the non-dominant hand to temporarily unlock the measuring device, allowing the hollow member to slide with respect to the measurement member.

Figure 3A:
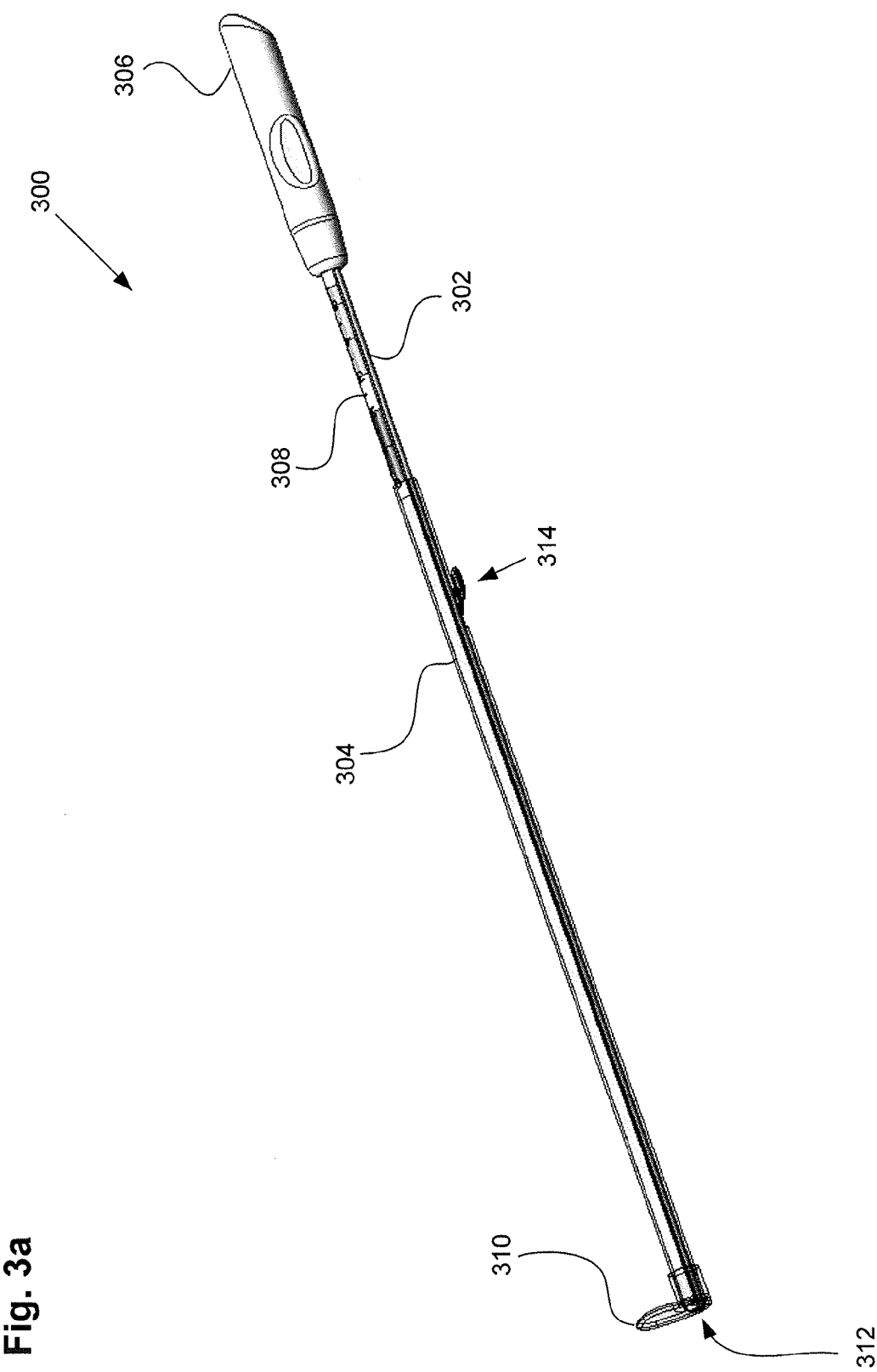
FIG. 3a is an illustration of a measuring device, according to one embodiment.

Referring now to FIG. 3a, yet another embodiment of a measuring device 300 is shown. Measuring device 300 includes many of the features of measuring device 100, described above and illustrated in FIGS. 1a-1e. For example, measuring device 300 includes an elongated measurement member 302 slidably disposed within an elongated hollow member 304. Handle 306 can be positioned on a proximal portion of the measuring device, and measurement scale 308, such as a color-coded measurement scale, can be disposed on the measurement member 302. The measuring device can further include a flange 310 on a distal portion of the device, and an opening 312 that allows the measurement member 302 to extend distally beyond the hollow member 304.

As described above, the device 300 can have a starting configuration, as shown in FIG. 3b, and a measuring configuration, as shown in FIG. 3c. In addition, a locking mechanism 314 can be located on the measuring device 300 that allows a user to secure the measurement member 302 within the hollow member 304 after the measurement of a body part, such as, e.g., the length of the cervix.

In FIG. 3d, the locking mechanism 314 includes button 316, cantilever arm 318, and detents 320. When the locking mechanism is in the locked configuration, as shown in FIG. 3d, the cantilever arm 318 engages detents 320 on the outside of measurement member 302. The cantilever arm can be integral to the hollow member 304, for example. To allow sliding of the measurement member within the hollow member, button 316 can be pressed inwards, causing cantilever arm 318 to disengage detents 320 and allow sliding.

For example, to take a measurement of a body part, a user can insert the measuring device 300 into the patient. The user can then press the button 316 inwards to disengage the cantilever arm and allow the measurement member to slide within the hollow member. After the measurement of a body part is taken with the device, the user can release the button, causing the cantilever arm to engage the detents and lock the position of the measurement member 302 within the hollow member 304. This allows the user to remove the device from the patient to read the measurement scale while ensuring that movement of the measurement member 302 proximally or distally within the hollow member 304 is prevented.

During a measurement procedure, a user can hold handle 306 with the dominant hand like a dart, and can hold the barrel of the hollow member 304 with the non-dominant hand. The user can activate button 316 with the non-dominant hand to temporarily unlock the measuring device, allowing the hollow member to slide with respect to the measurement member.

Referring now to FIG. 4a, another embodiment of a measuring device 400 is shown. Measuring device 400 includes many of the features of measuring device 100, described above and illustrated in FIGS. 1a-1e. For example, measuring device 400 includes an elongated measurement member 402 slidably disposed within an elongated hollow member 404. Handle 406 can be positioned on a proximal portion of the measuring device, and measurement scale 408, such as a color-coded measurement scale, can be disposed on the measurement member 402. The measuring device can further include a flange 410 on a distal portion of the device, and an opening 412 that allows the measurement member 402 to extend distally beyond the hollow member 404.

Figure 4B:
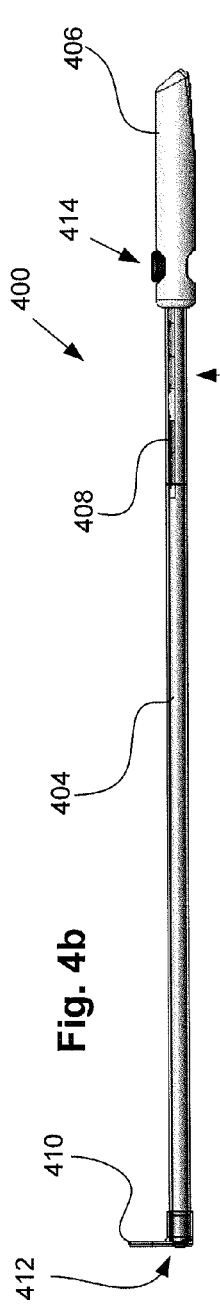
Figure 4C:
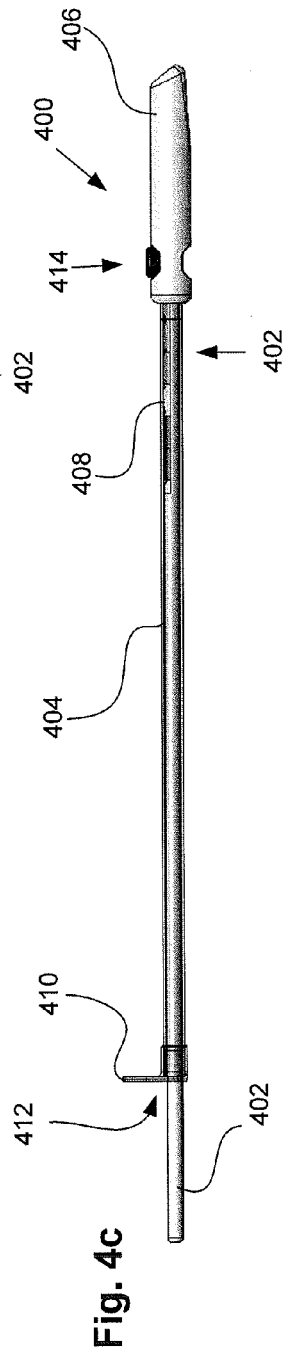

As described above, the device 400 can have a starting configuration, as shown in FIG. 4b, and a measuring configuration, as shown in FIG. 4c. In contrast to the embodiments described above, the hollow member 404 of the measuring device 400 in FIGS. 4a-4e slides into the handle 406 when a measurement is taken. The measurement member 402 remains fixed in position with respect to the handle, which allows the measurement member to extend distally beyond the flange 410 during measurements.

Figure 4D:
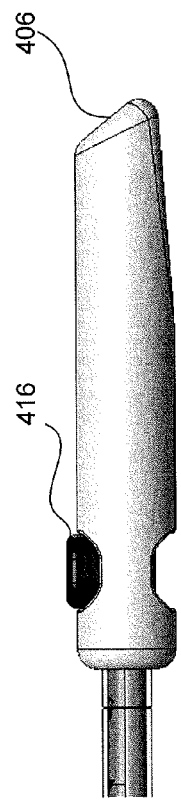
Figure 4E:
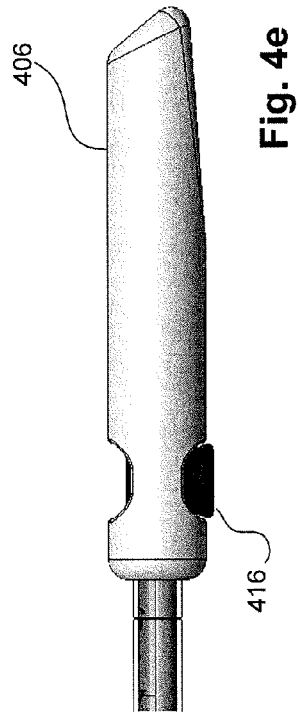

The measuring device 400 can further include a locking mechanism 414. The locking mechanism allows a user to lock the hollow member 404 within the handle 406, to prevent movement of the hollow member with respect to the measurement member after a measurement is taken. In the embodiment shown in FIGS. 4a-4e, the locking mechanism 414 can comprise a button 416 with a through-hole (not shown). In FIG. 4d, the device is shown in an unlocked configuration, in which the through-hole is aligned with the hollow member 404 to allow the hollow member to travel therethrough. When the device is in a locked configuration, as shown in FIG. 4e, the through-hole pushes against the hollow member, preventing movement of the hollow member with respect to the measurement member.

Figure 4F:
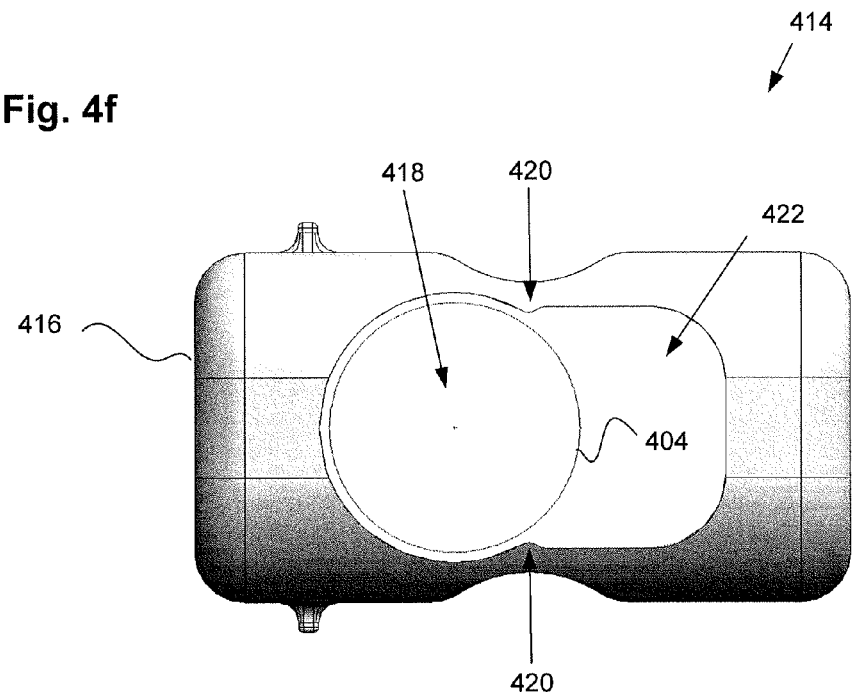
Figure 4G:
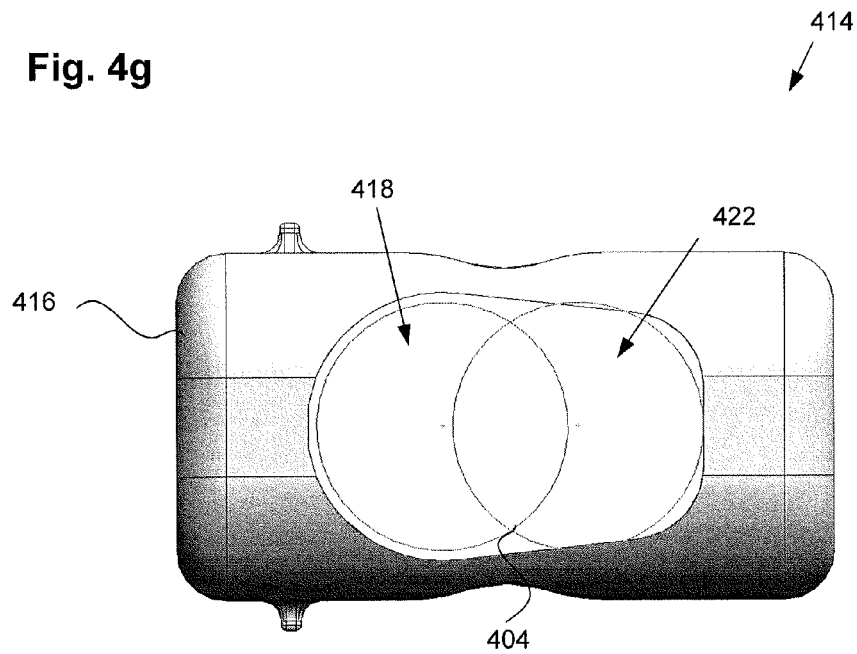

FIG. 4f shows a cross-sectional view of locking mechanism 414, button 416, and hollow member 404. The button geometry is designed to operate smoothly with a low actuation force to engage the locking mechanism. The open channel 418 of the button allows the hollow member 404 to slide freely into the handle when a measurement is being taken. When the button is depressed, the lock ramps 420 are forced to slide over the hollow member 404, which provides tactile and audible feedback that the device is in the locked position. The design of the lock ramps, including height and ramp angle affects the effort levels required to activate the button. The width of the lock channel 422 is designed to be narrower than the overall outside diameter of the hollow member 404, so that the interference between the two surfaces provides a retention force to maintain the measurement while the device is removed from the patient. In some embodiments, the locking mechanism does not include the lock ramps 420. In other embodiments, the lock channel 422 can be tapered to provide a frictional, locking fit for hollow member 404 when button 416 is depressed, as shown in FIG. 4g.

For example, to take a measurement of a body part, a user can insert the measuring device 400 in an unlocked configuration (e.g., where the through-hole is aligned to allowed movement of the hollow member) into the patient. After the measurement of a body part is taken with the device, the user can press the button 416, causing the through-hole to press against the hollow member to prevent movement of the hollow member. This allows the user to remove the device from the patient to read the measurement scale while ensuring that movement of the measurement member 402 proximally or distally within the hollow member 404 is prevented.

During a measurement procedure, a user can hold handle 406 with the dominant hand like a dart, and can hold the barrel of the hollow member 104 with the non-dominant hand. After taking a measurement, the user can activate button 416 with the dominant hand to lock the measuring device, preventing the hollow member from sliding with respect to the measurement member.

Figure 5A:
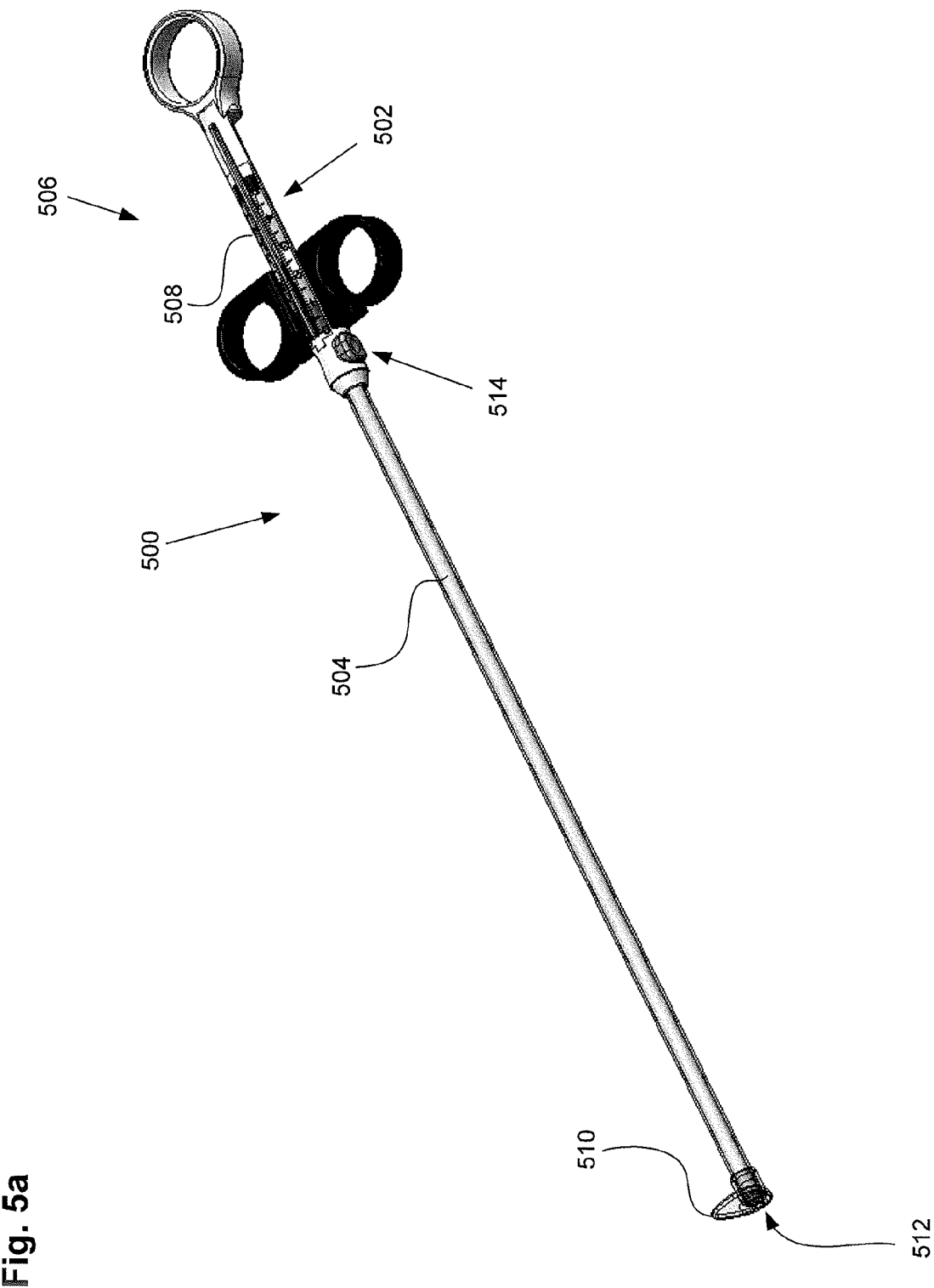
FIG. 5a is an illustration of a measuring device, according to one embodiment.

Referring now to FIG. 5a, another embodiment of a measuring device 500 is shown. Measuring device 500 includes many of the features of measuring device 100, described above and illustrated in FIGS. 1a-1e. For example, measuring device 500 includes an elongated measurement member 502 slidably disposed within an elongated hollow member 504. Syringe-style handle 506 can be positioned on a proximal portion of the measuring device, and measurement scale 508, such as a color-coded measurement scale, can be disposed on the measurement member 502. The measuring device can further include a flange 510 on a distal portion of the device, and an opening 512 that allows the measurement member 502 to extend distally beyond the hollow member 504.

Figure 5B:
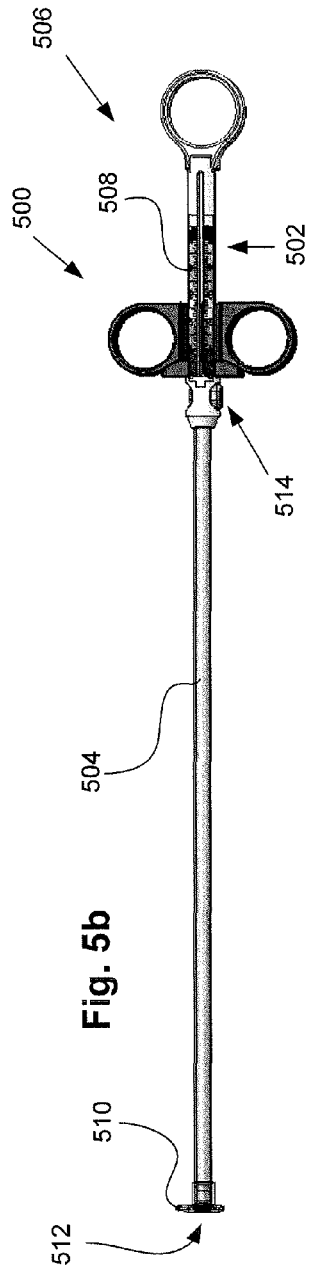
Figure 5C:
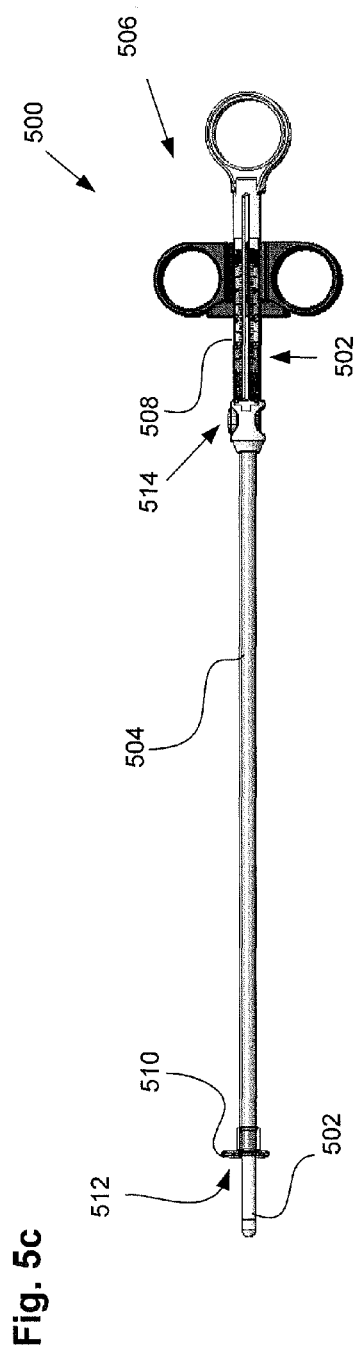

As described above, the device 500 can have a starting configuration, as shown in FIG. 5b, and a measuring configuration, as shown in FIG. 5c. Similar to the embodiment of measuring device 400 described above and illustrated in FIGS. 4a-4e, the hollow member 504 of the measuring device 500 in FIGS. 5a-5d slides into the handle 506 when a measurement is taken. The measurement member 502 remains fixed in position with respect to the handle, which allows the measurement member to extend distally beyond the flange 510 during measurements.

The measuring device 500 can further include a locking mechanism 514. The locking mechanism allows a user to lock the hollow member 504 within the handle 506, to prevent movement of the hollow member with respect to the measurement member after a measurement is taken. In the embodiment shown in FIG. 5d, the locking mechanism 514 can comprise a button 516 with a through-hole (not shown). Similar to the embodiments described above in FIGS. 4a-4e, the device can have an unlocked configuration, in which the through-hole is aligned with the hollow member 504 to allow the hollow member to travel therethrough. The device can also have a locked configuration, in which the through-hole pushes against the hollow member thereby preventing movement of the hollow member with respect to the measurement member.

Figure 5D:
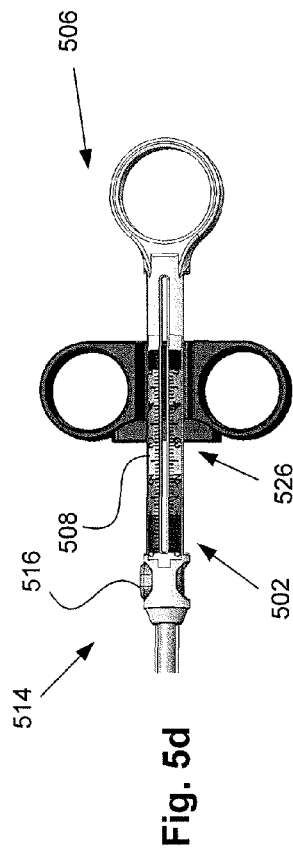

To take a measurement of a body part, a user can insert the measuring device 500 in an unlocked configuration (e.g., where the through-hole is aligned to allowed movement of the hollow member) into the patient. After the measurement of a body part is taken with the device, the user can press the button 516, causing the through-hole to press against the hollow member to prevent movement of the hollow member. This allows the user to remove the device from the patient to read the measurement scale while ensuring that movement of the measurement member 502 proximally or distally within the hollow member 504 is prevented. In FIG. 5d, the measurement scale is read at point 526 on the handle when taking the measurement, for example.

During a measurement procedure, a user can hold syringe-style handle 506 with the dominant hand like a syringe, and can hold the barrel of the hollow member 504 with the non-dominant hand. After taking a measurement, the user can activate button 516 with the dominant or non-dominant hand to lock the measuring device, preventing the hollow member from sliding with respect to the measurement member.

Figure 6A:
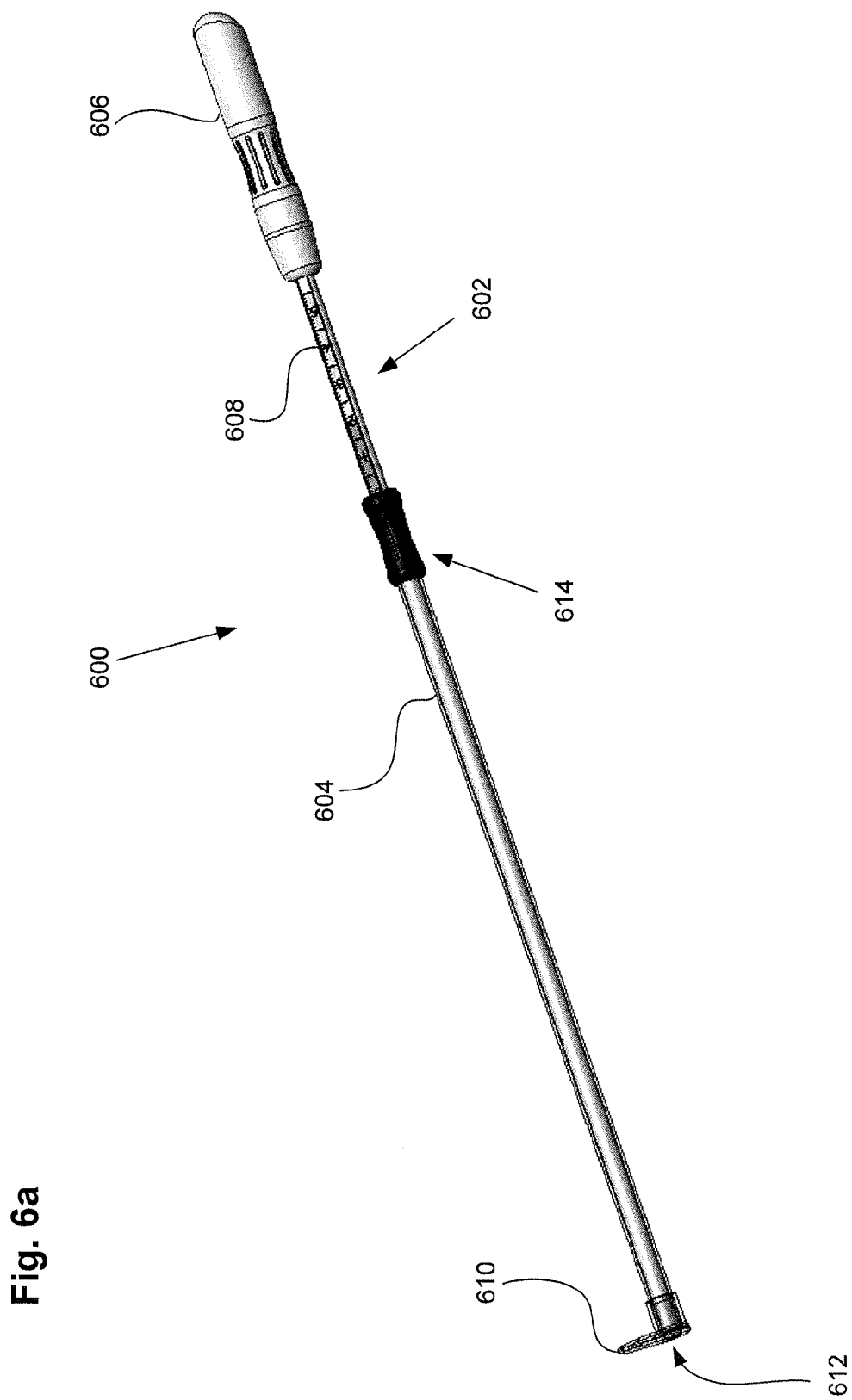
FIG. 6a is an illustration of a measuring device, according to one embodiment.

Referring now to FIG. 6a, another embodiment of a measuring device 600 is shown. Measuring device 600 includes many of the features of measuring device 100, described above and illustrated in FIGS. 1a-1e. For example, measuring device 600 includes an elongated measurement member 602 slidably disposed within an elongated hollow member 604. Handle 606 can be positioned on a proximal portion of the measuring device, and measurement scale 608, such as a color-coded measurement scale, can be disposed on the measurement member 602. The measuring device can further include a flange 610 on a distal portion of the device, and an opening 612 that allows the measurement member 602 to extend distally beyond the hollow member 604.

As described above, the device 600 can have a starting configuration, as shown in FIG. 6b, and a measuring configuration, as shown in FIG. 6c. The measuring device 600 can further include a locking mechanism 614. The locking mechanism allows a user to lock the measurement member 602 within the hollow member 604, to prevent movement of the measurement member with respect to the hollow member after a measurement is taken. In the embodiment shown in FIGS. 6a-6f, the locking mechanism 614 is disposed on the hollow member 204.

Referring now to FIG. 6d, which is a cross sectional view of the locking mechanism 614, the locking mechanism can further an annular snap 628. The measurement member 602 also has an annular snap 630 that corresponds to the annular snap 628 on the locking mechanism. When the locking mechanism is in an unlocked configuration, as shown in FIG. 6d, the annular snaps 628 and 630 are not in contact, so there is some play between the locking mechanism 614 and the measurement member 602, which allows the measurement member to slide freely within the hollow member 604. As a user rotates the locking mechanism, as shown in FIG. 6e, the annular snaps contact each other, providing the user with tactile feedback of locking. In FIG. 6f, the locking mechanism is shown in a locked configuration, with the annular snaps contacting each other on both sides. When the annular snaps are in contact as shown in FIG. 6f, there is no play between the hollow member and the measurement member, which prevents movement of the hollow member with respect to the measurement member.

To take a measurement of a body part, a user can insert the measuring device 600 into the patient in the unlocked configuration. After the measurement of a body part is taken with the device, the user can rotate the locking mechanism 614, causing the annular snaps to engage each other on both sides to lock the position of the measurement member 602 within the hollow member 604. This allows the user to remove the device from the patient to read the measurement scale while ensuring that movement of the measurement member 602 proximally or distally within the hollow member 604 is prevented.

During a measurement procedure, a user can hold handle 606 with the dominant hand like a dart, and can hold the locking mechanism 614 with the non-dominant hand. After taking a measurement, the user can rotate the locking mechanism with the non-dominant hand until the annular snaps engage each other to lock the measuring device, preventing the hollow member from sliding with respect to the measurement member. The user can also hold steady the locking mechanism 614 with the non-dominant hand and rotate the handle 606 with the dominant hand until the annular snaps engage each other to lock the measuring device. The relative motion of the locking mechanism 614 and the handle 606 is what engages the locking mechanism, regardless of which is held in place and which is rotated.

Figure 7A:
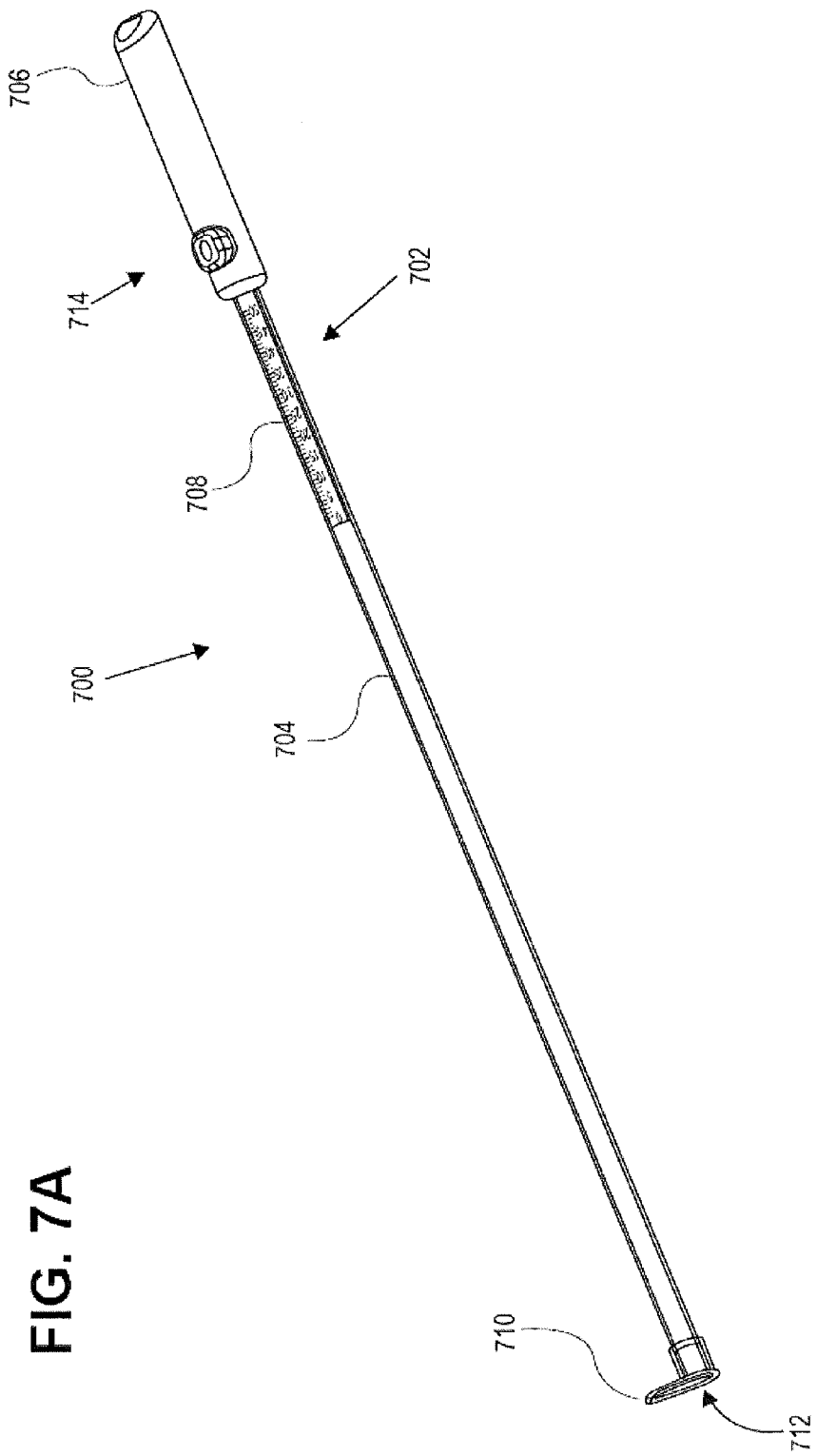
FIG. 7a is an illustration of a measuring device, according to one embodiment.

Referring now to FIG. 7a, another embodiment of a measuring device 700 is shown. Measuring device 700 includes many of the features of measuring device 100, described above and illustrated in FIGS. 1a-1e. For example, measuring device 700 includes an elongated measurement member 702 slidably disposed within an elongated hollow member 704. The measuring device can further include a flange 710 on a distal portion of the elongated hollow member 704, and an opening 712 that allows the measurement member 702 to extend distally beyond the hollow member 704. Handle 706 can be positioned on a proximal portion of the measuring device and can be attached to the measurement member and measurement scale 708 can be disposed on the measurement member 702. As shown in FIG. 7f, the measurement scale can be a millimeter sale, with markings from 0-50 mm, marked in 5 mm increments. Moreover, the background 732 for the measurement scale 708 can be opaque. For example, the measurement member 702 can be composed of an opaque material or an opaque coating can cover the portion of the measurement member 702 on which the measurement scale 708 is printed. An opaque background for the measurement scale can allow for easier readability of the numbers on the scale. Further, the hollow member 704 can be transparent and include an indicator line 734 that is colored, e.g., blue, to help contrast it from the measurement scale. Contrasting the indicator line 734 with the measurement scale allows for easier readability of the final measurement.

Figure 7B:
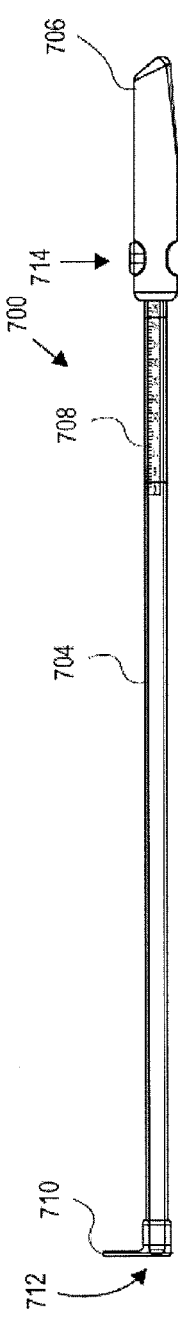
Figure 7C:
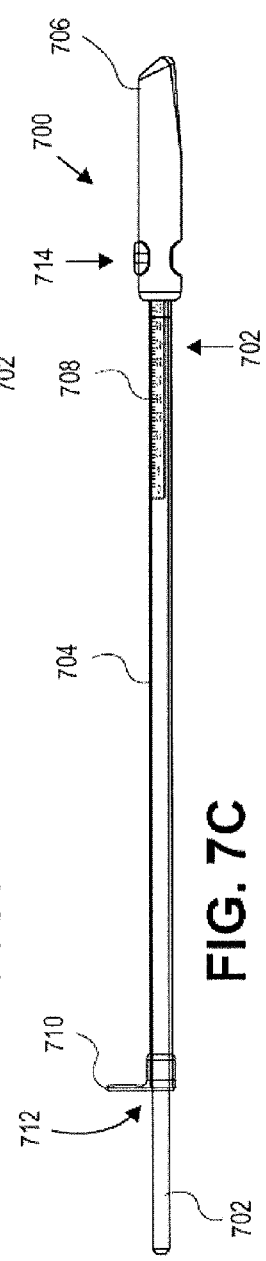
Figure 7D:
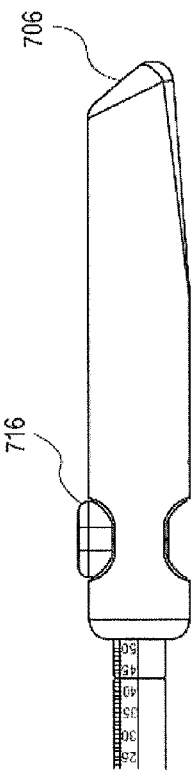
Figure 7E:
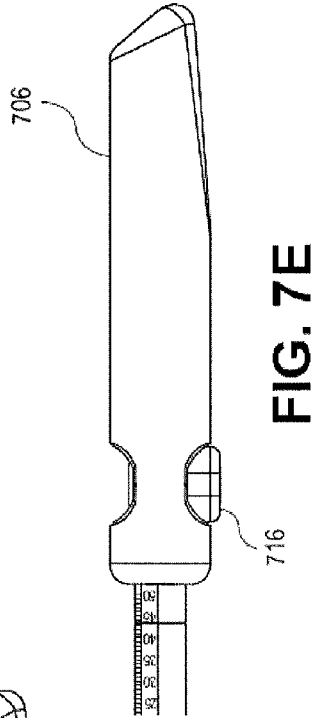
Figure 7F:
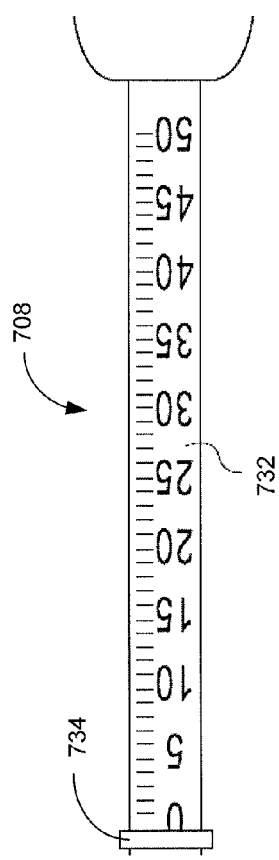
Figure 7G:
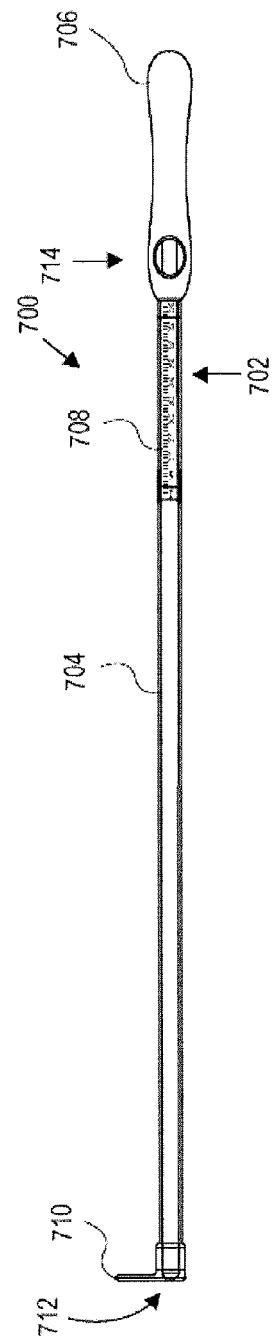
Figure 7H:
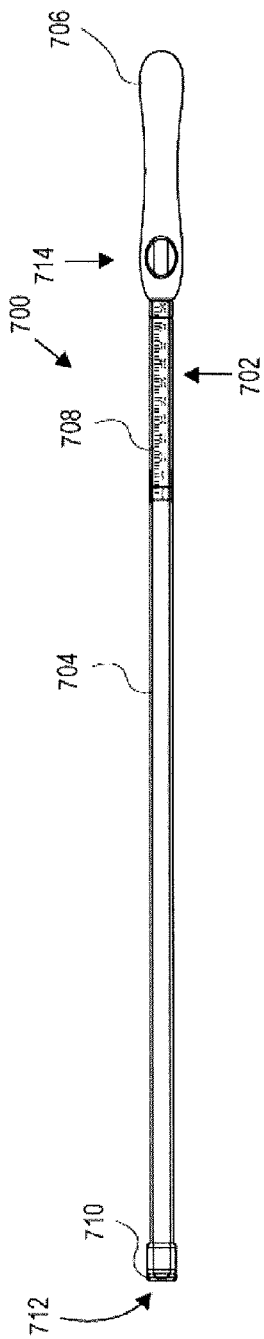

As described above, the device 700 can have a starting configuration, as shown in FIG. 7b, and a measuring configuration, as shown in FIG. 7c. Similar to the embodiment of measuring device 400 described above and illustrated in FIGS. 4a-4e, the hollow member 704 of the measuring device 700 in FIGS. 7a-7d slides into the handle 706 (or, alternatively, the handle 706 slides over the hollow member 704) when a measurement is taken. The measurement member 702 remains fixed in position with respect to the handle, which allows the measurement member to extend distally beyond the flange 710 during measurements. As shown in FIGS. 7g and 7h, the elongated hollow member 704 can be free to rotate with respect to the handle 706 and the measurement member 702 (FIG. 7g shows the flange 710 extending parallel to the page, while FIG. 7h shows the flange 710 extending out of the page). Such free rotation allows for the accommodation of any measurement technique, e.g. right or left-handed measurements, while still allowing for proper placement of the flange 710. That is, rotation of the hollow member 702 to place the flange 710 in a desired position allows the measurement scale to remain in place, i.e., facing the user. Maintaining the measurement scale directed towards the users ensures that the user is more easily able to read and determine the measured length.

The measuring device 700 can further include a locking mechanism 714. The locking mechanism allows a user to lock the hollow member 704 within the handle 706, to prevent rotational or longitudinal movement of the hollow member with respect to the measurement member after a measurement is taken. In the embodiment shown in FIG. 7d, the locking mechanism 714 can comprise a button 716 with a through-hole (not shown). Similar to the embodiments described above in FIGS. 4a-4e, the device can have an unlocked configuration, in which the through-hole is aligned with the hollow member 704 to allow the hollow member to travel therethrough. The device can also have a locked configuration, in which the through-hole pushes against the hollow member thereby preventing movement of the hollow member with respect to the measurement member.

To take a measurement of a body part, a user can hold the handle 706 with the dominant hand and can hold the hollow member 704 with the non-dominant hand. The user can orient the measuring scale 708 such that it faces the user and can then rotate the hollow member 704 such that the flange 710 is properly oriented with respect to the patient. Because the hollow member 704 is transparent, the measuring scale 708 can be viewed through the hollow member 704.

The measuring device 700 can be inserted in an unlocked configuration (e.g., where the through-hole is aligned to allowed movement of the hollow member) into the patient. After the measurement of a body part is taken with the device, as described above, the user can press the button 716, causing the through-hole to press against the hollow member to prevent movement of the hollow member. This allows the user to remove the device from the patient to better read the measurement scale while ensuring that movement of the measurement member 702 proximally or distally within the hollow member 704 is prevented.

Figure 8:
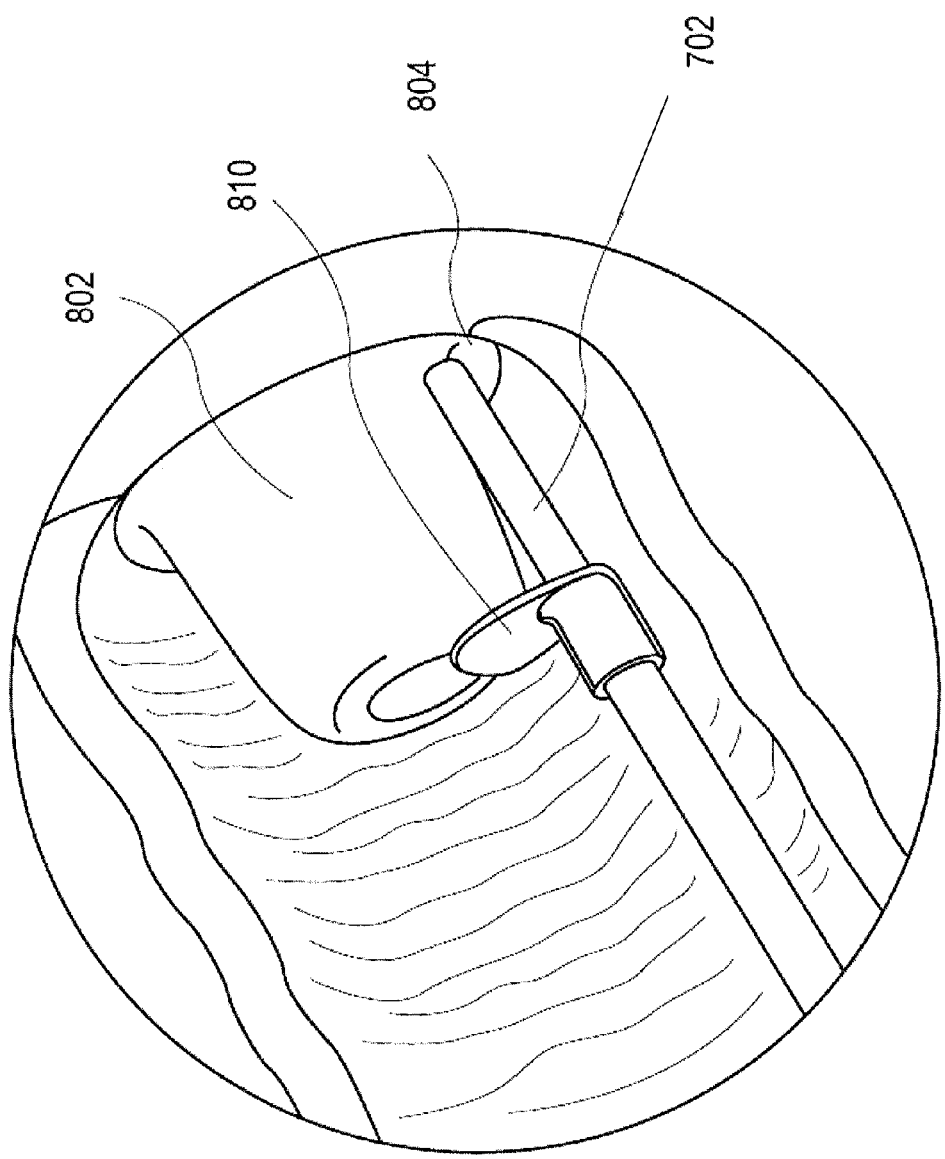
FIG. 8 is an illustration of a measuring device in use for measuring the vaginal cervix.

Referring to FIG. 8, the devices described herein can be used to measure the vaginal cervical length. The flange 810 (representing any of the flanges described herein) can be placed against the proximal wall of cervix 802, while the measurement member 702 (representing any of the measurement members described herein) can be extended along the lateral wall of the cervix 802 until it is stopped by the vaginal fornix 804. The measurement member 702 and the flange 810 can then be locked with respect to one another such that the device's measurement scale can be used to determine the length as described above.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A device for measuring a length of a cervix, comprising:
   an elongate measurement member extending along a longitudinal axis and including a measurement scale thereon;
   a hollow member coaxial with a disposed over the elongate measurement member, the hollow member comprising a transparent portion configured to allow viewing of the measurement scale therethrough;
   a flange offset from the longitudinal axis and attached to a distal end of the hollow member, the hollow member being freely rotatable about the longitudinal axis relative to the elongate measurement member to place the flanged in a desired location without moving the measurement scale; and
   a handle attached to the proximal end of the elongate measurement member, the hollow member configured to slide into the handle.

2. The device of claim 1, wherein the flange has an opening through which the elongate measurement member can advance distally.

3. The device of claim 1, wherein the flange has a flat surface perpendicular to the longitudinal axis.

4. The device of claim 1, wherein the measurement scale is a millimeter scale.

5. The device of claim 1, further comprising an indicator line on the hollow member.

6. The device of claim 1, wherein the elongate measurement member is configured to extend distally beyond the flange when the hollow member is moved axially.

7. The device of claim 1, wherein the measurement scale extends from 0 mm to 50 mm.

8. The device of claim 7, wherein the scale is marked in 5 mm increments.

9. The device of claim 1, wherein the measurement scale includes an opaque background.

10. The device of claim 9, wherein the indicator line is a color other than black.

11. The device of claim 9, wherein the indicator line is configured to slide over the measurement scale to indicate a distance between a distal end of the elongate measurement member and the flange.

12. A method for measuring a length of a cervix, comprising:
   holding a handle of a device such that a measurement scale of an elongate measurement member attached to the handle faces up towards the user;
   rotating a hollow member that is coaxial with and disposed over the elongate measurement member relative to the elongate measurement member;
   advancing the device distally within a vagina until a flange on a distal end of the hollow member contacts a proximal wall of the cervix;
   advancing the elongate measurement member distally within the vagina along a lateral wall of the cervix until a distal end of the elongate measurement member contacts a vaginal fornix, wherein advancing the elongate measurement member distally comprises pushing the handle distally such that the hollow member slides into the handle; and
   observing a position of the hollow member relative to the measurement scale through a transparent portion of the hollow member to determine a length of the cervix in the fornix vaginae.

13. The method of claim 12, wherein observing the position comprises observing an indicator line on the hollow member with respect to the measurement scale.

14. The method of claim 12, further comprising determining the risk of miscarriage based upon the length of the cervix in the fornix vaginae, wherein the length of the cervix in the fornix vaginae is inversely related to the risk of miscarriage.

15. The method of claim 12, further comprising predicting the ease of inducing labor, wherein the length of the cervix in the fornix vaginae is inversely related to the ease of inducing labor.

16. The method of claim 12, further comprising determining the risk of preterm labor based upon the length of the cervix in the fornix vaginae, wherein the length of the cervix in the fornix vaginae is inversely related to the risk of preterm labor.

17. The method of claim 12, wherein the flange is offset from a longitudinal axis of the elongate measurement member.

18. The method of claim 12, further comprising locking the elongate measurement member relative to the hollow member.

19. The method of claim 18, wherein the holding and locking steps are performed with the same hand.

* * * * *